United States Patent
Shiomi et al.

(10) Patent No.: US 11,353,453 B2
(45) Date of Patent: Jun. 7, 2022

(54) HYDROPHILIC COLORED CELLULOSE MICROPARTICLES

(71) Applicant: Asahi Kasei Kabushiki Kaisha, Tokyo (JP)

(72) Inventors: Yoshiyuki Shiomi, Tokyo (JP); Atsushi Horii, Tokyo (JP); Takeshi Matsuse, Tokyo (JP); Ken Muraoka, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 264 days.

(21) Appl. No.: 16/498,736

(22) PCT Filed: Mar. 28, 2018

(86) PCT No.: PCT/JP2018/012938
§ 371 (c)(1),
(2) Date: Sep. 27, 2019

(87) PCT Pub. No.: WO2018/186267
PCT Pub. Date: Oct. 11, 2018

(65) Prior Publication Data
US 2021/0109093 A1    Apr. 15, 2021

(30) Foreign Application Priority Data

Apr. 6, 2017 (JP) .............................. JP2017-076162

(51) Int. Cl.
*G01N 33/548* (2006.01)
*G01N 33/58* (2006.01)
(Continued)

(52) U.S. Cl.
CPC ..... *G01N 33/548* (2013.01); *G01N 33/54386* (2013.01); *G01N 33/587* (2013.01); *B82Y 5/00* (2013.01); *G01N 2458/00* (2013.01)

(58) Field of Classification Search
CPC ............... G01N 33/587; G01N 33/548; G01N 33/54386; G01N 33/543; G01N 33/54353;
(Continued)

(56) References Cited

U.S. PATENT DOCUMENTS 4,143,203 A * 3/1979 Rigopulos .............. A61K 39/44
428/403
2007/0099814 A1    5/2007 Tamori et al.
(Continued)

FOREIGN PATENT DOCUMENTS

CN    102604305 A    7/2012
JP    2009-168495 A    7/2009
(Continued)

OTHER PUBLICATIONS

Mears et al., Solvent relaxation NMR measurements on polymer, particle, surfactant systems. Langmuir 1998, 14, 997-1001 (Year: 1998).*
(Continued)

*Primary Examiner* — Bao-Thuy L Nguyen
*Assistant Examiner* — Xiaoyan Zou
(74) *Attorney, Agent, or Firm* — Morgan, Lewis & Bockius LLP

(57) ABSTRACT

Provided are: a coloring cellulose microparticle enabling false positive to be significantly reduced while maintaining a high detection sensitivity; and an immunochromatographic diagnostic kit using the same.

5 Claims, 1 Drawing Sheet

(51) Int. Cl.
*G01N 33/543* (2006.01)
*B82Y 5/00* (2011.01)

(58) Field of Classification Search
CPC ........ G01N 2458/00; G01N 33/54313; B82Y 5/00

See application file for complete search history.

(56) References Cited

U.S. PATENT DOCUMENTS

| | | | |
|---|---|---|---|
| 2011/0020954 A1* | 1/2011 | Shiomi | G01N 33/548 436/530 |
| 2012/0225496 A1 | 9/2012 | Yoshida | |
| 2015/0111307 A1* | 4/2015 | Yoshida | G01N 33/585 436/501 |
| 2015/0118675 A1 | 4/2015 | Ito | |
| 2015/0293082 A1 | 10/2015 | Shiomi et al. | |
| 2016/0123974 A1 | 5/2016 | Horii et al. | |
| 2017/0045510 A1 | 2/2017 | Ito et al. | |

FOREIGN PATENT DOCUMENTS

| | | |
|---|---|---|
| JP | 2012-181181 A | 9/2012 |
| JP | 2014-163758 A | 9/2014 |
| JP | 2016-191658 A | 11/2016 |
| WO | 90/15666 A1 | 12/1990 |

OTHER PUBLICATIONS

International Preliminary Report on Patentability and Written Opinion issued in corresponding International Patent Application No. PCT/JP2018/012938 dated Oct. 17, 2019.

Supplementary European Search Report issued in European Patent Application No. 18781015.5 dated Feb. 24, 2020.

Goddard et al., "Polymer surface modification for the attachment of bioactive compounds," Progress in Polymer Science, 32: 698-725 (2007).

* cited by examiner

HYDROPHILIC COLORED CELLULOSE MICROPARTICLES

FIELD

The present invention relates to colored cellulose microparticles having a hydrophilic layer on the surface of the microparticles and carboxyl groups introduced onto the surface of the microparticles with spacers interposed there between, and to a diagnostic kit and in vitro diagnostic drug using the same.

BACKGROUND

A technology capable of easily and rapidly determining the presence or absence of diseases, pathogens and the like has been sought after in recent years in the health care and food fields. Various technologies have been developed to respond to this need. It is currently possible to easily and rapidly carrying out various examinations such as those for infections by influenza and other pathogens, pregnancy tests, examinations for the presence of cancer markers or muscle markers, or examinations for the presence of allergenic substances present in foods or substances causing food poisoning. Numerous measurement methods have been developed for use with these technologies such as immunochromatographic assay, fluorescence immunochromatographic assay, enzyme immunoassay, latex agglutination assay or chemiluminescence assay. Among these, immunochromatographic assays, which enable results to be determined visually, are widely used since they are characterized by not requiring any special devices or specialized knowledge and enable diagnoses to be made easily and rapidly. For example, pregnancy tests, which are a type of immunochromatographic assay, can be purchased at ordinary pharmacies and offer consumers a high degree of general-purpose use.

Immunochromatographic assays (to be referred to as "immunochromatography") utilize an antigen-antibody reaction and consists of sandwich assays and competitive assays. The measurement methods are broadly divided into a lateral flow method, in which the substance to be detected is developed in the horizontal direction on a membrane, and a flow through method, in which the substance to be detected is developed in the vertical direction. From the viewpoint of simplicity, a method is widely used that consists of capturing antigen with antibody using a sandwich assay with the flow through method. The measurement procedure consists of the steps indicated below.

(i) An antibody that reacts with an antigen or other substance to be detected is immobilized on a membrane such as a nitrocellulose membrane at a specific site (test line).

(ii) A detection reagent that supports the antibody that reacts with the detection target on a labeling substance referred to as a colored particle is prepared and coated onto a conjugate pad and dried followed by combining with the aforementioned membrane, a sample pad and an absorbent pad to prepare an immunochromatography kit.

(iii) A developing solution, which is mixed with a sample desired to be examined for the presence of antigen, is dropped onto the sample pad and the presence of color in the test line (TL) is observed visually (or using a simple immunochromatography reader) to determine the presence or absence of antigen. In the case antigen is present in the sample, the test line becomes colored.

In general, in many cases in which results are determined visually, qualitative analyses are used that only make it possible to determine whether or not the detection target in the form of antigen is present or absent.

Examples of coloring particles used in immunochromatography include the colloidal gold particles disclosed in the following PTL1 and the colored latex disclosed in the following PTL2. The problem with these coloring particles is that, due to the hydrophobic properties of the surface of the microparticles, a phenomenon known as nonspecific adsorption ends up occurring in which biomolecules such as proteins are adsorbed. When nonspecific adsorption occurs, there is the risk of the occurrence of false positives, considered to be the major problem associated with immunochromatography. A false positive refers to the test line being colored even though a detection target is not present in a sample. Since the occurrence of a false positive can lead to misdiagnosis, it is essential to not allow the occurrence of false positives when releasing an immunochromatography kit commercially. One of the mechanisms behind the occurrence of false positives is thought to be due to the coloring particle being adsorbed to the antibody coated on the test line through a substance that has been non-specifically adsorbed to the coloring particle. Therefore, the following PTL3 discloses that false positives are reduced as a result of non-specific adsorption being suppressed by a technique consisting of binding hydrophilic polyethylene glycol (PEG) to the hydrophobic surface of colloidal gold. However, in this method, the antibody-antigen reaction is inhibited by the steric structure of the PEG chain on the surface of the microparticles, thereby resulting in the risk of a decrease in detection sensitivity. In this manner, there are many cases in which measures taken to reduce false positives ends up causing a decrease in detection sensitivity.

With the foregoing in view, the following PTL4 discloses that an extremely high level of detection sensitivity was achieved by chemically bonding colored cellulose microparticles to antibodies. Since these microparticles are derived from cellulose, although the surface is slightly hydrophilic in comparison with colloidal gold, since the surface is still hydrophobic, there is the possibility of the occurrence of nonspecific adsorption, thereby still retaining the risk of the occurrence of false positives in the same manner as conventional coloring particles.

As has been described above, there is still a need to provide technology for reducing false positives while maintaining high detection sensitivity, and as one way to respond to this need, there is a strong desire for the development of coloring particles that are capable of considerably suppressing nonspecific adsorption without inhibiting the antibody-antigen reaction.

CITATION LIST

Patent Literature

PTL1: International Publication No. WO 2015/163384 A1
PTL2: Japanese Unexamined Patent Publication No. 2009-168495
PTL3: International Publication No. WO 2013/141122 A1
PTL4: International Publication No. WO 2011/062157 A1

SUMMARY

Technical Problem

With the foregoing in view, an object of the present invention is to provide coloring particles capable of considerably reducing false positives while maintaining high detection sensitivity.

Solution to Problem

As a result of conducting extensive studies to solve the aforementioned problems, the inventors of the present invention found that cellulose microparticles can be obtained that are surprisingly able to reduce nonspecific adsorption of proteins and other biomolecules by imparting a hydrophilic layer to the surface of the microparticles and introducing carboxyl groups onto the surface of the microparticles with spacers interposed there between, and confirmed that immunochromatography using these as coloring particles is capable of considerably reducing false positives while maintaining high detection sensitivity, thereby leading to completion of the present invention.

Namely, the present invention is as indicated below.

[1] Colored cellulose microparticles having an average particle diameter of 60 nm to 900 nm, having coloring intensity of 1.0 to 10.0, having a hydrophilic layer on the surface of the microparticles, and having carboxyl groups introduced onto the surface of the microparticles with spacers interposed there between.

[2] The colored cellulose microparticles described in [1] above, wherein the amount of the carboxyl groups introduced is 0.20 mmol to 3.00 mmol per gram of the aforementioned colored cellulose microparticles.

[3] The colored cellulose microparticles described in [1] or [2] above, wherein the hydrophilic layer is any of a silane layer, a polyethylene glycol (PEG) layer or a mixed layer of a silane layer and a polyethylene glycol (PEG) layer.

[4] The colored cellulose microparticles described in any of [1] to [3] above, wherein the spacers are hydrocarbon-based structures.

[5] A structure in which a ligand is covalently bonded to the carboxyl groups of the colored cellulose microparticles described in any of [1] to [4] above.

[6] An immunochromatographic diagnostic kit containing the structure described in [5] above.

Advantageous Effects of Invention

The colored cellulose microparticles according to the present invention are capable of considerably reducing false positives while maintaining high detection sensitivity if used as coloring particles of immunochromatography since non-specific adsorption of biomolecules is reduced.

DESCRIPTION OF EMBODIMENTS

Figure 1:
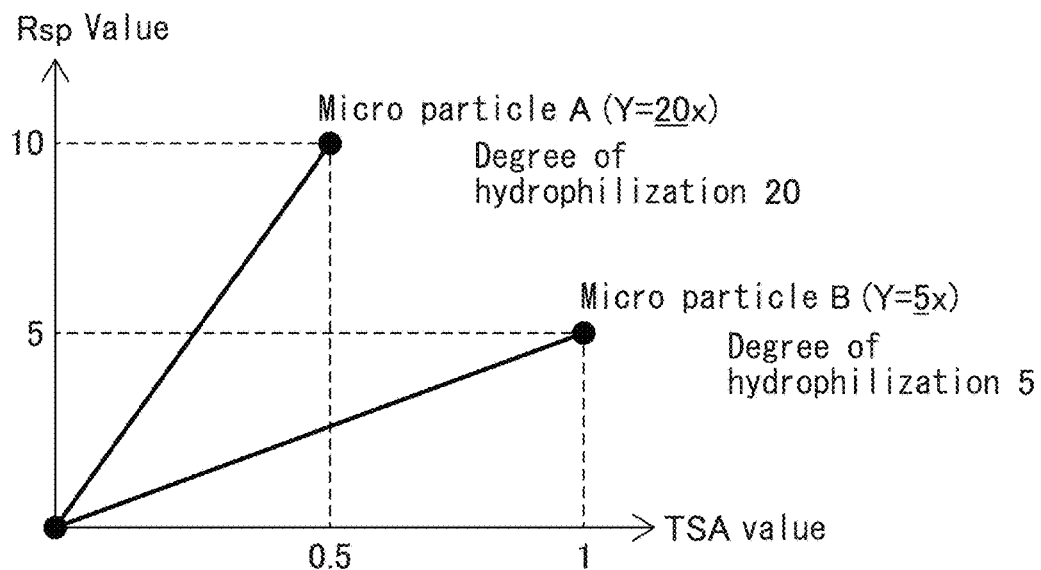
FIG. 1 is a graph indicating a plot of rate of change in relaxation time (Rsp value) versus microparticle total surface area (TSA value) for determining degree of hydrophilization.

The inventors of the present invention unexpectedly and surprisingly found that an effect that considerably reduces false positives and maintenance of high detection sensitivity are possible by combining a prescribed hydrophilic layer and a prescribed spacer on colored cellulose microparticles.

As is disclosed in PTL4, detection sensitivity was determined to improve as a result of chemically bonding an antibody with colored cellulose microparticles having a large particle diameter and deep color. However, due to the inadequate hydrophilicity of the surface of these microparticles, the microparticles are susceptible to the occurrence of non-specific adsorption of proteins and other biomolecules, thereby resulting in the risk of the occurrence of false positives when using for immunochromatography. Therefore, although measures such as adding an additive such as a surfactant to the developing solution were implemented to reduce false positives, these resulted in a simultaneous decrease in detection sensitivity. The inventors of the present invention thought that it might be possible to reduce false positives while maintaining high detection sensitivity by making the microparticles per se resistant to nonspecific adsorption and making it possible to introduce large amounts of antibody onto the surface of the microparticles. As a result of repeatedly conducting experiments based on this hypothesis, the inventors of the present invention found that high detection sensitivity can be maintained while considerably reducing false positives by imparting a hydrophilic layer to the surface of colored cellulose microparticles and introducing a large amount of carboxyl groups onto the surface of the microparticles with hydrocarbon-based spacers interposed there between, thereby making it possible to introduce a large amount of antibody onto the microparticles while reducing nonspecific adsorption of proteins and other biomolecules on the surface of the microparticles.

As is disclosed in PTL3, false positives were determined to be able to be reduced by imparting a hydrophilic layer to the surface of microparticles. On the other hand, hydrocarbon-based compounds are typically said to easily adsorb proteins and other biomolecules causing false positives. With the foregoing in view, the inventors of the present invention unexpectedly found that false positives can be reduced considerably by combining a hydrocarbon-based hydrophobic spacer in addition to imparting a hydrophilic surface. Without desiring to be bound by a specific theory, the inventors of the present invention believe that they succeeded in considerably reducing false positives since hydrocarbon-based spacers rise from the surface of the microparticles as a result of being repelled by the hydrophilic layer and are densely introduced onto the surface of the microparticles due to the hydrophobic interaction between spacers, and when gaps allowing the entrance of proteins and other biomolecules causing false positives onto the surface of the microparticles are eliminated and nonspecific adsorption is suppressed, or in other words, although proteins causing false positives are unable to be adsorbed onto the sides of the linear, hydrocarbon-based spacers as a result of the spacers being disposed roughly in parallel rows on the surface of the microparticles, antibodies are able to covalently bond to carboxyl groups on the ends of the spacers.

The following provides a detailed explanation of the present embodiment.

The colored cellulose microparticles of the present embodiment are characterized by having an average particle diameter of 60 nm to 900 nm, having coloring intensity of 1.0 to 10.0, having a hydrophilic layer on the surface of the microparticles, and having carboxyl groups introduced onto the surface of the microparticles with spacers interposed there between.

The term "average particle diameter" refers to the volume-average median diameter in the case of having measured by dynamic light scattering. In the present embodiment, the average particle diameter is within the range of 60 nm to 900 nm. If the average particle diameter is within this range, the test line becomes deeper, or in other words, detection sensitivity increases, in the case of using in immunochromatography due to the increased surface area of the microparticles. If the average particle diameter is less than 60 nm, coloring intensity per microparticle decreases due to the decrease in surface area, thereby resulting in lower detection sensitivity or the occurrence of microparticle aggregation. On the basis thereof, the lower limit of particle diameter is preferably 70 nm and more preferably 80 nm. On the other hand, since the pores of the membrane end up becoming clogged if the microparticle diameter exceeds 900 nm, more time is required for diagnosis or the surface of the membrane may be colored after testing, thereby having a detrimental effect on evaluation of test results or resulting in poor detection sensitivity. On the basis thereof, the upper limit of particle diameter is preferably 800 nm and more preferably 700 nm. Furthermore, the average particle diameter mentioned here is only intended to be an average value, and a portion of the distribution of particle diameter may be outside the aforementioned range.

The reason for using volume average for particle diameter is that, although excessively large microparticles end up clogging the membrane during immunochromatography, since the effects of large microparticles are enhanced in the case of using volume average, even if only a slight number of large particles are present, the effect thereof is reflected in the result. There are also various other ways to represent average in addition to volume average such as number average or area average. Naturally the value of particle diameter changes when the method used to represent particle diameter differs.

The term "coloring intensity" refers to a value that defines the depth of color of the microparticles prior to antibody binding after having introduced a reactive group, and in the present embodiment, is within the range of 1.0 to 10.0. The larger this value, the deeper the color of the microparticles and the higher the detection sensitivity in the case of using in immunochromatography. Naturally, as this value becomes larger, various methods can be employed for coloring such as using a deep-colored dye, increasing the number of dyeing cycles, coupling through some type of compound serving as a spacer, facilitating the uptake of dye by increasing the amorphous region of the microparticles, or facilitating the uptake of dye by making the microparticles porous. However, when considering economy, the upper limit of coloring intensity is preferably 7.0 and more preferably 5.0. In addition, since detection sensitivity during immunochromatography decreases as the value becomes smaller, the lower limit of color intensity is preferably 1.5 and more preferably 2.0.

The method used to measure coloring intensity consists of preparing a pure water dispersion of microparticles of a known concentration, measuring visible absorbance using an integrating sphere over a range of 400 nm to 800 nm at an optical path length of 10 mm, measuring the peak value of the resulting absorbance (ABS) curve, dividing back the resulting value by the weight percentage of the coloring particles and defining as the value obtained by converting to absorbance per 0.01% by weight of the coloring particles. For example, when the concentration of the prepared microparticles is 0.0045% by weight and the peak value of the absorbance curve is 1.0, then the coloring intensity becomes $(1 \times 0.01) \div 0.0045 = 2.2$.

The reason for measuring visible absorbance using an integrating sphere when measuring the color depth of the microparticles is to be able to measure the color depth of the microparticles when dispersed in a liquid most accurately. Although a method consisting of drying the microparticles and then measuring the resulting solid with a colorimeter has been employed as a method for measuring the color depth of microparticles, this method is unable to accurately measure the color depth of microparticles. Since color tone and maximum wavelength differ among metal colloids, for example, according to particle diameter, color depth cannot be accurately reflected between dry aggregated microparticles and those in a dispersed state. In addition, even though microparticles may be dispersed in a liquid at the same concentration, color depth decreases once aggregation has occurred. Moreover, the reason for using an integrating sphere when measuring visible absorbance is to remove effects attributable to scattering of the microparticles per se. Ordinary measurement of visible absorbance consists of measuring transmitted light, and not only effects attributable to absorbance of color light components from the incident light, but also effects attributable to scattering of the microparticles per se, are reflected in measurement of absorbance. For example, although the colloidal gold typically used in immunochromatography is used at a particle diameter of 40 nm to 60 nm and may occasionally be used at a particle diameter of 100 nm, there are hardly any effects of scattered light due to the small particle diameter in any of these cases. In contrast, latex particles have a considerable effect on scattering light due to the large particle diameter thereof. Based on these reasons, visible absorbance measurement using an integrating sphere is used to more accurately reflect color depth of the microparticles per se even in cases in which particle diameters or particle materials differ.

The term "hydrophilic layer" refers to a layer composed of a structure having high hydrophilicity as the name implies that is chemically bonded to hydroxyl groups of the microparticles. There are no particular limitations on the structure of this hydrophilic layer and a silane layer, polyethylene glycol (PEG) layer or phosphorylcholine layer and the like can be used. A mixture of two of the aforementioned layers may also be used depending on the case. For example, a layer can be formed that contains a silane layer and a PEG layer at a ratio of 1:1. The silane layer referred to here is a layer formed by bonding hydroxyl groups of the particles to a structure containing Si groups. Similarly, a PEG layer and phosphorylcholine layer refer to layers in which hydroxyl groups of the particles are bonded to structures containing PEG groups and phosphorylcholine groups, respectively. From the viewpoint of subsequent bondability with the reactant, one of the structures that form the hydrophilic layer preferably contains an amino group. Whether or not a hydrophilic layer has been formed is determined by a method such as infrared spectroscopy, microscopic observation or elemental analysis.

Furthermore, in the present description, a "spacer" differs from the "hydrophilic layer" in that the spacer bonds with a reactive group present in the "hydrophobic layer".

There are no particular limitations on the hydrophilizing agent used to impart the hydrophilic layer, and specific examples thereof include the following: vinyltrimethoxysilane, vinyltriethoxysilane, 2-(3,4-epoxycyclohexyl)ethyltrimethoxysilane, 3-glycidoxypropylmethyldimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypiropyltriethoxysilane, 3-acryloxypropyltrimethoxysilane, N-2-(aminoethyl)-3-aminopropylmethyldimethoxysilane, N-2-(aminoethyl)-3-aminopropyltrimethoxysilane, 3-aminopropyltrimethoxysilane, 3-aminopropyltriethoxysilane, 3-triethoxysilyl-N-(1,3-dimethyl-butyidene)propylamine, N-phenyl-3-aminopropyltrimethoxysilane, 3-mercaptopropylmethyldimethoxysilane, 3-mercaptopropyltrimethoxysilane, 3-isocyanatopropyltrimethoxysilane, polyethylene glycol trimethoxysilane, polyethylene glycol triethoxysilane, amino-PEG12-propionic acid, amino-PEG8-propionic acid, amino-PEG4-propionic acid, poly (ethylene glycol)-2-aminoethyl ether acetic acid, FMOC-PEG 5k-succinimide butanoate, HO-PEG 5k-NHS, O-[2-(Fmoc-amino)-ethyl]-O'-2-carboethyl)polyethylene glycol, polyethylene glycol bis(amine) and 1-O-octadecyl-2-O-methyl-sn-glycero-3-phosphorylcholine. Among these, preferable examples include N-2-(aminoethyl)-3-aminopropylmethyldimethoxysilane, N-2-(aminoethyl)-3-aminopropyltrimethoxysilane, 3-aminopropyltrimethoxysilane, 3-aminopropyltriethoxysilane, 3-triethoxysilyl-N-(1,3-dimethyl-butylidene)propylamine, amino-PEG12-propionic acid, amino-PEG8-propionic acid, amino-PEG4-propionic acid, poly(ethylene glycol)-2-aminoethyl ether acetic acid and polyethylene glycol bis(amine), and more preferable examples include N-2-(aminoethyl)-3-aminopropylmethyldimethoxysilane, N-2-(aminoethyl)-3-aminopropyltrimethoxysilane, 3-aminopropyltrimethoxysilane, 3-aminopropyltriethoxysilane and 3-triethoxysilyl-N-(1,3-dimethyl-butylidene)propylamine.

In the case of using a hydrophilic layer containing amino groups, the amount of reactive amino groups remaining after having introduced carboxyl groups is preferably less than 0.20 mmol per gram of colored cellulose microparticles. If within this range, not only it is possible to suppress adsorption of hydrophobic substances, but since adsorption of hydrogen bonding substances can also be suppressed, the adsorbed amount of biomolecules can be drastically reduced. If the amount of reactive amino groups remaining after having introduced carboxyl groups is 0.20 mmol or more per g of colored cellulose microparticles, the effect of reducing false positives is diminished due to an increase in adsorption by hydrogen bonding in particular. On the basis of the above, the upper limit of the amount of residual reactive amino groups is preferably 0.15 mmol and more preferably 0.10 mmol.

Fluorescence assay is used to measure the amount of residual reactive amino groups. A fluorescence reagent is used that emits light only in the case of having reacted with an amino group. First, a calibration curve is created for the relationship between amount of amino groups and luminous intensity using samples having known amounts of amino groups. Subsequently, the fluorescence reagent is reacted with the microparticles. The fluorescence intensity of the microparticles is then measured to obtain the luminous intensity thereof. The resulting luminous intensity is then entered into the calibration curve to calculate the amount of amino groups.

"Degree of hydrophilization" is defined as an indicator that represents the degree of hydrophilization of the hydrophilic layer. In the present description, the "degree of hydrophilization" refers to the ease of wetting of the microparticle surface, or in other words, is an indicator that represents affinity for water. The degree of hydrophilization is measured by pulsed NMR. Pulsed NMR is an analytical technique consisting of exciting the protons of water molecules by irradiating a microparticle dispersion with radio waves followed by measuring the amount of time until the protons return to the ground state (relaxation time). Relaxation time becomes shorter since water molecules adsorbed to the microparticle surface suppress mobility, while relaxation time become longer since there is little suppression of mobility by bulk water molecules (water molecules not adsorbed to the microparticle surface), thereby allowing the water molecules to move freely. Thus, the relaxation time of a microparticle dispersion determined by pulsed NMR changes according to the ratio between water molecules adsorbed to the microparticle surface and bulk water molecules. Namely, the higher the hydrophilicity of the microparticle surface, the greater the number of water molecules that are able to be adsorbed on the surface, thereby shortening relaxation time.

The Minispec mq20 system manufactured by Bruker Corporation is used for measurement by pulsed NMR. After stirring a microparticle dispersion having a concentration of 1% (wt/vol), 0.5 mL are transferred to a glass NMR tube having an outer diameter of 10 mm followed by placing in an NMR apparatus set to 30° C. and measuring each type of parameter after setting in the manner indicated below.

Observed nucleus: $^1H$
Measured relaxation time: Transverse relaxation time T2 (ms)
Measurement mode: CPMG method
Integration cycles: 32
Recycle delay: 10 (s)
90°-180° pulse separation (τ): 2 (ms)
Total number of acquired echoes: 2000 points The resulting magnetization decay curve (curve indicating time-based changes in magnetization intensity) was fit to the following equation (1) according to the least squares method using the exponential approximation function of Microsoft Excel:

$$M(t)=M_0 \cdot \exp(-t/T2) \qquad \text{Equation (1)}$$

(wherein, M(t) represents signal strength at a certain time t, $M_0$ represents the initial value of signal strength, and T2 represents relaxation time).

In order to calculate the degree of hydrophilization from the measured relaxation time, a graph is prepared in which the rate of change in relaxation time (Rsp value) is plotted on the vertical axis and the total surface area (TSA value) of the microparticles is plotted on the horizontal axis followed by creating an approximation curve using the least squares method and defining the slope of that curve as the degree of hydrophilization.

Calculation of Rsp Value:

$$Rsp \text{ value}=Rav \div Rb-1$$

(wherein Rav represents an average relaxation time constant (reciprocal of relaxation time of sample) and Rb represents a relaxation time constant of bulk microparticles (reciprocal of relaxation time of water blank).

Calculation of TSA value ($m^2$)

$$TSA \text{ value}=SA \times V \times \Psi_p \times \rho$$

(wherein, SA represents microparticle specific surface area ($m^2/g$)=6÷ρ×d), where p represents microparticle density (g/$cm^3$) (microparticle density: 1.4 g/$cm^3$, latex particle density: 1.0 g/$cm^3$, colloidal gold particle density: 19.3 g/$cm^3$), d represents microparticle diameter (μm), V represents NMR tube volume of the portion irradiated with radio waves ($cm^3$) (≈ amount of sample), $\psi_p$ represents microparticle volume ratio, where microparticle volume (i)=microparticle concentration (wt %)÷100÷microparticle density, water volume (ii)=(1−microparticle volume (i))÷water density (0.997 g/$cm^3$) and ψp (microparticle volume ratio) =microparticle volume (i)÷water volume (ii), with p having the same meaning as previously described).

For example, as shown in FIG. 1, values of microparticle A (TSA value: 0.5, Rsp value: 10) and microparticle B (TSA value: 1, Rsp value: 5) were plotted on a graph to create their respective approximation curves using the least squares method. In the case of microparticle A, Y=20x, while in the case of microparticle B, Y=5x. The microparticle having the larger slope of the approximation curve (degree of hydrophilization), namely microparticle A, was determined to have a larger degree of hydrophilization.

In the present embodiment, the degree of hydrophilization is preferably within the range of 30.0 to 200.0. If the degree of hydrophilization is within this range, in addition to the microparticles being able to easily move through the membrane due to the surface thereof being hydrophilic, the amount of proteins and the like that adhere to the microparticle surface decreases. As a result, the number of false positives occurring when using in immunochromatography decreases. What is more, since microparticles having a degree of hydrophilization within this range are such that the hydrophilic layer unexpectedly functions as a protective layer, there is less susceptibility of decreases in coloring intensity during introduction of carboxyl groups. Consequently, since the microparticles are able to withstand harsh reaction conditions, it is possible to introduce a larger number of carboxy groups. As a result, since a large number of antibodies can also be supported on the microparticles, microparticles can be obtained that maintain high detection sensitivity. If the degree of hydrophilization is less than 30.0, since the microparticle surface becomes hydrophobic, proteins and the like end up being adsorbed onto the microparticle surface resulting in increased susceptibility to the occurrence of false positives. In addition, flow through the membrane becomes poor resulting in longer diagnosis times. In addition, if the degree of hydrophilization is less than 30.0, since there is increased susceptibility to decreases in coloring density of the microparticles during the carboxyl group introduction reaction, density sensitivity ends up decreasing. On the basis of the above, the lower limit of the degree of hydrophilization is more preferably 35.0 and even more preferably 40.0. On the other hand, if the degree of hydrophilization exceeds 200.0, since hydrogen bonding becomes dominant, the amount of proteins and other biomolecules adsorbed increases, and since this results in the risk of the occurrence of false positives, the upper limit of the degree of hydrophilization is more preferably 190.0 and even more preferably 180.0.

The term "spacer" refers to a chemical group that connects a microparticle with a carboxyl group through the "hydrophilic layer". In the present embodiment, although the "spacer" bonds with reactive groups of the "hydrophilic layer", the "hydrophilic layer" bonds with hydroxyl groups of the microparticles. For example, in the case of having reacted C18-bromostearic acid through a silane layer bonded to the microparticles, the hydrophilic layer becomes the silane layer while the spacer becomes $(CH_2)_{17}$. There are no particular limitations on the structure of the spacer and a hydrophobic structure such as a hydrocarbon-based structure in the manner of alkyl groups, alkene groups, alkane groups or benzene rings can be used. Although there are no particular limitations on the number of carbon atoms, from the viewpoint of being able to realize improved sensitivity without being affected by the electric double layer of the particle surface, the number of carbons is preferably 3 or more. In general, since a hydrophobic structure is effective in suppressing adsorption of biomolecules, a hydrophilic spacer such as PEG is frequently used for colloidal gold, latex particles or silica particles and the like since the surface of the microparticles is hydrophobic in these cases. For example, Nagasaki, et al. reported that nonspecific adsorption can be reduced considerably by introducing different lengths of PEG chains onto a gold surface (see Nagasaki, et al., Polymer, Vol. 61, No. 2, 2012). This is because hydrophobic spacers such as hydrocarbon-based spacers are thought result in the spacers becoming adhered to the microparticle surface due to hydrophobic interaction. Consequently, reactivity between carboxyl groups and antibodies becomes poor and the required amount of antibody is unable to be immobilized on the microparticles, thereby resulting in the risk of a decrease in detection sensitivity. In addition, hydrophobic structures are generally likely to undergo hydrophobic interaction with proteins and the like. In other words, the use of a hydrophobic structure for the spacer causes proteins and other biomolecules to be adsorbed resulting in a high possibility of the occurrence of false positive. In contrast, the inventors of the present invention defied this common knowledge and surprisingly succeeded in considerably reducing the adsorbed amount of biomolecules responsible for the occurrence of false positives by combining the hydrophilic layer of the microparticle surface with a hydrophobic spacer such as a hydrocarbon-based spacer, and confirmed that false positives can be significantly reduced while maintaining detection sensitivity. Since a hydrophilic layer is present on the microparticle surface, if the spacer is hydrophilic, interaction of hydrogen bonds and the like with the hydrophilic layer is thought to occur. Consequently, the spacer ends up being adsorbed on the hydrophilic layer thereby preventing the required amount of antibody from being immobilized on the microparticles, which in addition to causing a decrease in detection sensitivity, also prevents suppression of false positives from being achieved as a result of being unable to decrease the adsorbed amount of biomolecules. On the other hand, in an embodiment that used hydrophobic spacers such as hydrocarbon-based spacers, not only were the spacers not adsorbed to the hydrophilic layer, but the spacers were aligned in an orderly manner and were reliably introduced onto the microparticles without any gaps there between, and this is thought to have eliminated gaps where biomolecules are able to approach the microparticle surface or spacers and enabled the adsorbed amount of biomolecules to be reduced considerably, thereby making it possible to considerably reduce false positives.

For example, as shown in the following Table 1, in contrast to the incidence of false positives of Example 15 that used a PEG chain being 1%, the incidence of false positives of Example 2 that used a hydrophobic spacer was 0%, in contrast to the incidence of false positives of Example 17 that uses a PEG chain being 1%, the incidence of false positives of Example 1 that used a hydrophobic spacer was 0%, in contrast to the incidence of false positives of Example 18 that used a PEG chain being 2%, the incidence of false positives of Example 16 that used a hydrophobic spacer was 1%, and in contrast to the incidence of false positives of Example 20 that used a PEG chain being 2%, the incidence of false positives of Example 19 that used a hydrophobic spacer was 1%.

A method such as infrared spectroscopy, elemental analysis, nuclear magnetic resonance (NMR) or mass spectrometry (MS) can be used to identify the spacer. For example, the spacer portion can be detached from the microparticles by reacting a strong acid or strong base with the microparticles introduced with carboxyl groups at a high temperature. Subsequently, the microparticles can be separated by centrifugation and the like and the supernatant can be measured by NMR or MS to identify the structure of the spacer.

The term "introduced amount of carboxyl groups" refers to the amount of carboxyl groups introduced per gram of colored cellulose microparticles. The introduced amount thereof is preferably 0.20 mmol/g to 3.00 mmol/g. By making the introduced amount to be within this range, antibody or protein and the like used for the blocking agent can be chemically bonded to the microparticles both firmly and in large amount, thereby making it possible to realize both high sensitivity and reduction of false positives. If the introduced amount is less than 0.20 mmol/g, since the bonded amount of antibody or other protein is inadequate, there is the risk of a decrease in detection sensitivity if false positive reduction measures such as the addition of additives are employed. Moreover, if the introduced amount is less than 0.20 mmol/g, the distance between introduced carboxyl groups becomes excessively large, thereby resulting in an increased likelihood of carboxyl groups that did not react with antibody and the like inducing hydrogen bonding between molecules instead of within molecules. In other words, there is the risk of the occurrence of false positives as a result of protein and the like being adsorbed through hydrogen bonds. Consequently, the lower limit of the introduced amount of carboxyl groups is preferably 0.25 mmol/g and more preferably 0.30 mmol/g. On the other hand, if the introduced amount exceeds 3.00 mmol/g, since the weight per particle increases, coloring intensity per microparticle decreases. Since there is the risk of a decrease in detection sensitivity during use in immunochromatography if coloring intensity decreases, the upper limit is preferably 2.50 mmol/g and more preferably 2.00 mmol/g.

Examples of methods used to calculate introduced amount include fluorometry, neutralization titration and infrared spectroscopy. In the present embodiment, fluorometry is primarily used to accurately measure the amount of carboxyl groups able to react with antibody and protein. A fluorescence reagent is used that emits light only in the case of having reacted with a carboxyl group. First, a calibration curve is prepared for the relationship between the amount of carboxyl groups and luminous intensity using samples having known amounts of carboxyl groups. Subsequently, the fluorescence reagent is reacted with the microparticles. The fluorescence intensity of the microparticles is then measured to obtain luminous intensity. The resulting luminous intensity is then entered into the calibration curve to calculate the amount of carboxyl groups.

Although there are no particular limitations on the carboxylating agent used when introducing carboxyl groups, specific examples thereof include the following: 2-bromoacetic acid, 3-bromopropionic acid, 4-bromobutyric acid, 5-bromopentanoic acid, 6-bromohexanoic acid, 7-bromoheptanoic acid, 8-bromooctanoic acid, 11-bromoundecanoic acid, 18-bromostearic acid, 16-heptadecenoic acid, 5-hexanoic acid, epichlorhydrin, 4-aminobutyric acid, 3-aminopropionic acid, 5-aminopentanoic acid, 6-aminohexanoic acid, 7-aminoheptanoic acid, 8-aminooctanoic acid, adipic acid, eicosanedioic acid, 1,8-octanedicarboxylic acid, 1,4-butanedicarboxylic acid, 1,6-hexanedicarboxylic acid, 2-chloroacetic acid, 3-chloropropionic acid, 4-chlorobutyric acid, 5-chloropentanoic acid, 6-chlorohexanoic acid, 7-chloroheptanoic acid, 8-chlorooctanoic acid, 11-chloroundecanoic acid, 18-chlorostearic acid, amino-PEG12-propionic acid, amino-PEG8-propionic acid, amino-PEG4-priopionic acid, α,w-bis[2-{(3-carboxy-1-oxypropyl)amino}ethyl]polyethylene glycol, HO-PEG12-COOH, HO-PEG12-propionic acid, HO-PEG8-propionic acid, 0-(2-carboxyethyl)polyethylene glycol, COOH-PEG12-COOH, poly(ethylene glycol) bis(carboxymethyl) ether, propionic acid-PEG12-propionic acid, propionic acid-PEG8-propionic acid and propionic acid-PEG4-propionic acid. Among these, preferable examples include 3-bromopropionic acid, 4-bromobutyric acid, 5-bromopentanoic acid, 6-bromohexanoic acid, 7-bromoheptanoic acid, 8-bromooctanoic acid, 11-bromoundecanoic acid, 18-bromostearic acid, adipic acid, eicosanedioic acid, 1,8-octanedicarboxylic acid, 1,4-butanedicarboxylic acid and 1,6-hexanedicarboxylic acid, and more preferable examples include 8-bromooctanoic acid, 11-bromoundecanoic acid, 18-bromostearic acid, adipic acid, eicosanedioic acid and 1,8-octanedicarboxylic acid.

In the present description, a "microparticle" refers to a structure in which the major axis (L) and minor axis (D) are nearly equal and the shape is nearly spherical. More specifically, the L/D ratio as represented by L÷D is 1.0 to 3.0. If the value of L/D is within this range, there is less susceptibility to the occurrence of clogging in the case of using as an immunochromatographic diagnostic kit, and the value of L/D is more preferably 1.0 to 2.0, even more preferably 1.0 to 1.5 and most preferably 1.0 to 1.3. L/D is measured by capturing an electron micrograph of the particles, measuring the major axis (L) and minor axis (D) for 100 particles, and then calculating the average value of the 100 particles.

There are no particular limitations on the method used to produce the colored cellulose microparticles. Examples of methods used include a method consisting of first molding microparticles and then supporting a coloring component such as a pigment or dye thereon, a method consisting of molding microparticles and supporting smaller coloring microparticles such as a metal colloid or colorant thereon, and a method consisting of collectively adding a coloring component such as a pigment, dye, colorant or metal colloid during molding of microparticles followed by molding. Among these, the method consisting of first molding microparticles and then supporting a coloring component such as a pigment or dye thereon is preferable due to the ease of adjusting the characteristics of the microparticles, such as adjusting particle diameter, adjusting color depth, adjusting the type of color or adjusting the surface status of the microparticles. In addition, a dye is preferable for the supported coloring component due to the ease of being supported on the microparticles.

There are no particular limitations on the type of dye in the case of using a dye as a coloring component. Dyes such as reactive dyes, direct dyes, metal complexed dyes, acid dyes, basic dyes, disperse dyes, sulfur dyes, vegetable dyes, naphthol dyes or fluorescent dyes can be used. Naturally, any of these dyes may also be combined. Among these, reactive dyes that covalently bond with the hydroxyl groups of cellulose are particularly preferable in terms of stability and allowing a large amount of dye to be retained.

There are no particular limitations on the method used to mold the cellulose microparticles in the case of first molding cellulose microparticles followed by loading a coloring component thereon. Examples of methods used include a method consisting of physically refining natural cellulose with a ball mill or high-pressure homogenizer, a method consisting of refining by chemically treating with acid or base, and a method consisting of temporarily dissolving the cellulose in a good solvent and molding into particulate form. In addition, derivatized cellulose may also be dissolved and molded into particulate form followed by returning the derivatized substituents to hydroxyl groups to prepare cellulose microparticles. Moreover, these molding methods may be used in combination. In addition, there are no particular limitations on the type of cellulose, and cellulose such as regenerated cellulose, purified cellulose, natural cellulose or cellulose in which derivatized substituents have been returned to hydroxyl groups can be used. Among these, the method consisting of temporarily dissolving the cellulose in a good solvent and molding into particulate form is preferable from the viewpoints of adjusting particle diameter and adjusting particle shape, and regenerated cellulose is preferable for the type of cellulose.

There are no particular limitations on the type of good solvent used to dissolve the cellulose in the case of temporarily dissolving the cellulose in a good solvent followed by molding into particulate form, and various good solvents capable of dissolving cellulose can be used, such as cuprammonium solution, viscose solution, N-methylmorpholine or various types of ionic liquids. Among these, cuprammonium solution is preferable from the viewpoint of adjusting particle diameter or adjusting particle shape. In addition, there are also no particular limitations on the method used to mold the dissolved cellulose into particles. Phase separation was used in the present embodiment.

The term "ligand" refers to a substance having the property of selectively and specifically bonding to a specific test target substance. Although there are no particular limitations on the type thereof, examples include antibodies, enzymes, genes, hormones, nucleic acids, peptides and proteins.

The term "immunochromatographic diagnostic kit" refers to a product that uses an antigen-antibody reaction to easily detect the presence or absence of a test target substance present in various samples. The types of immunochromatographic diagnostic kits consist of lateral flow types and flow through types. Although there are no particular limitations on the type of kit provided it uses coloring particles and a sample pad, a lateral flow type is preferable. In addition, although lateral flow types consist of dipstick types and cassette types, there are no particular limitations thereon. There are no particular limitations on the composition of the immunochromatographic diagnostic kit and may be employ a composition typically used in the art. There are no particular limitations on the type of members other than the coloring particles and sample pad provided they are members used in the art, and examples thereof include a conjugate pad (including antibody-sensitized coloring particles), nitrocellulose or other membrane, adsorbent pad and mount. In addition, a portion of these members may be omitted as necessary.

A "diagnostic method" that uses the immunochromatographic diagnostic kit refers to various diagnoses carried out using the immunochromatographic diagnostic kit. There are no particular limitations on the diagnosis target, and can be various diagnosis targets such as those for humans, those for animals, those for foods, those for plants or other environmental testing. A typical diagnostic procedure consists of collecting a specimen sample from the test target, subjecting the sample to pretreatment such as extraction or filtration as necessary, dropping the sample onto the sample pad, waiting for a prescribed amount of time from the start of the test, and assessing the diagnosis result according to coloring that differs according to the presence or absence of the test target substance. The procedure is naturally not limited to this procedure, but rather can be applied to similar procedures or principle diagnosis. The test sample is preferably filtered in advance to make it possible to remove any excess foreign objects or contaminants, thereby making it possible to anticipate even shorter diagnosis times and improved diagnosis accuracy.

There are no particular limitations on the target able to be diagnosed with the immunochromatographic diagnostic kit, and specific examples include the following: cancer markers, hormones, infectious diseases, autoimmunity, serum proteins, TDM, coagulation and fibrinolysis, amino acids, peptides, proteins, genes and cells. More specifically, examples include CEA, AFP, ferritin, β2-microglobulin, PSA, CA19-9, CA125, BFP, esterase 1, pepsinogen 1,2, occult blood, urine β2-microglobulin, PIVKA-2, urine BTA, insulin, E3, HCG, HPL, LH, HCV antigen, HBs antigen, HBs antibody, HBc antibody, HBe antigen, HBe antibody, HTLV-1 antibody, HIV antibody, toxoplasma antibody, syphilis, ASO, type A influenza antigen, type A influenza antibody, type B influenza antigen, type B influenza antibody, rota antigen, adenovirus antigen, rota-adenovirus antigen, group A *Streptococcus*, group B *Streptococcus, Candida* antigen, CD, *Cryptococcus* antigen, cholera, *Meningococcus* antigen, granulocytic elastase, *Helicobacter pylori* antibody, O157 antibody, O157 antigen, *Leptospira* antibody, *Aspergillus* antigen, MRSA, RF, total IgE, LE test, CRP, IgG, A, M, IgD, transferrin, urine albumin, urine transferrin, myoglobin, C3-C4, SAA, LP(a), α1-AC, α1-M, haptoglobin, microtransferrin, APR score, FDP, D dimer, plasminogen, AT3, α2PI, PIC, PAI-1, protein C, coagulation factor X3, type IV collagen, hyaluronic acid, GHbA1c, various other types of antigens, various types of antibodies, various types of viruses, various types of bacteria, various types of amino acids, various types of peptides, various types of proteins, various types of DNA, various types of cells, various types of allergens, various types of residual agricultural chemicals and various types of toxic substances.

The following provides a description of examples of a method for preparing cellulose microparticles, a method for colored cellulose microparticles, a method for hydrophilizing cellulose microparticles, a method for introducing carboxyl groups and a method for preparing an immunochromatographic diagnostic kit. The present embodiment should naturally be understood as not being limited thereto.

[Method for Preparing Cellulose Microparticles]

Cellulose linter is dissolved in a good solvent of cellulose. A cuprammonium solution prepared using a known method is used for the good solvent. A mixed system consisting of an organic solvent, water and ammonia is mainly used for the coagulation liquid. The prepared cuprammonium cellulose solution is added while stirring this coagulation liquid to carry out coagulation. Moreover, a slurry containing the target cellulose microparticles can be obtained by adding sulfuric acid, neutralizing and regenerating the cellulose microparticles. At this time, the slurry becomes acidic due to acid that remains after using for regeneration, and since impurities such as ammonia generated during neutralization is also contained, a procedure is necessary for purifying to a cellulose dispersion comprising cellulose microparticles and medium. Treatment consisting of centrifugation, decantation and dilution with the liquid dispersion medium is used repeatedly for this purification procedure. Since the cellulose microparticles present in the resulting cellulose microparticle dispersion may aggregate during the course of the purification procedure, dispersion treatment by shearing and the like can be carried out in this case. A high-pressure homogenizer is used as a means for applying shearing.

[Method for Coloring Cellulose Microparticles]

Sodium sulfate and reactive dye are added to the resulting aqueous dispersion of cellulose microparticles following heating to a suitable temperature in a thermostatic chamber while stirring with a magnetic stirrer. After heating, base in the form of sodium carbonate is added to initiate dyeing.

After a prescribed amount of time has elapsed, a slurry containing the target colored cellulose microparticles can be obtained. Since the slurry is alkaline at this time and further contains sodium sulfate, unreacted dye and the like, a procedure is necessary for purifying to a colored cellulose microparticle dispersion comprised of the colored cellulose microparticles and medium. Purification is carried out by centrifugation in the same manner as previously described to obtain a colored cellulose microparticle dispersion. Since the colored cellulose microparticles present in the resulting colored cellulose microparticle dispersion may aggregate during the course of the purification procedure, dispersion treatment such as shearing can be carried out in this case. A high-pressure homogenizer is used as a means for applying shearing.

[Method for Hydrophilizing Colored Cellulose Microparticles]

An organic solvent and water are added to the resulting aqueous dispersion of colored cellulose microparticles followed by heating to a suitable temperature in a thermostatic chamber while stirring with a magnetic stirrer. After heating, a commercially available hydrophilizing agent is added to initiate the reaction. After a prescribed amount of time has elapsed, a slurry can be obtained that contains the target hydrophilized colored cellulose microparticles. Since the slurry is alkaline at this time and further contains unreacted hydrophilizing agent and the like, a procedure is necessary for purifying to hydrophilized colored cellulose microparticle dispersion comprised of the hydrophilized colored cellulose microparticles and medium. Purification is carried out by centrifugation in the same manner as previously described to obtain a hydrophilized colored cellulose microparticle dispersion. Since the hydrophilized colored cellulose microparticles present in the resulting hydrophilized colored cellulose microparticle dispersion may aggregate during the course of the purification procedure, dispersion treatment such as shearing can be carried out in this case. A high-pressure homogenizer is used as a means for applying shearing.

[Method for Introducing Carboxyl Groups into Hydrophilized Colored Cellulose Microparticles]

An organic solvent and base are added to the resulting aqueous dispersion of hydrophilized colored cellulose microparticles followed by heating to a suitable temperature in a thermostatic chamber while stirring with a magnetic stirrer. After heating, a reactant having carboxyl groups is added to initiate the reaction. After a prescribed amount of time has elapsed, a slurry can be obtained that contains the target carboxyl group-introduced hydrophilized colored cellulose microparticles. Since the slurry contains organic solvent, base or unreacted reactant at this time, a procedure is necessary for purifying to a carboxyl group-introduced hydrophilized colored cellulose microparticle dispersion comprised of the carboxyl group-introduced hydrophilized colored cellulose microparticles and medium. Purification is carried out by centrifugation in the same manner as previously described to obtain a carboxyl group-introduced hydrophilized colored cellulose microparticle dispersion. Since the carboxyl group-introduced hydrophilized colored cellulose microparticles present in the resulting carboxyl group-introduced hydrophilized colored cellulose microparticle dispersion may aggregate during the course of the purification procedure, dispersion treatment such as shearing can be carried out in this case. A high-pressure homogenizer is used as a means for applying shearing.

[Method for Preparing Immunochromatographic Diagnostic Kit]

A carboxyl group-introduced hydrophilized colored cellulose microparticle dispersion adjusted to a prescribed concentration is prepared followed by the addition of buffer and antibody and stirring for a prescribed amount of time while adjusting the temperature to bind the antibody to the carboxyl group-introduced hydrophilized colored cellulose microparticles. After stirring for a certain amount of time, a blocking agent is further added followed by stirring for a certain amount of time while adjusting the temperature to carry out blocking of the carboxyl group-introduced hydrophilized colored cellulose microparticles. Various blocking agents can be used for the blocking agent corresponding to such factors as the test target substance, specimen or composition of the solution used for the dilution thereof. Casein is particularly preferable for the blocking agent of the carboxyl group-introduced hydrophilized colored cellulose microparticles. Centrifugation is carried out to wash the carboxyl group-introduced hydrophilized colored cellulose microparticles following antibody binding and blocking, microparticles that have precipitated with the supernatant containing excess antibody and blocking agent are separated and the supernatant is removed by decantation. A liquid such as a buffer is added to the precipitated microparticles followed by carrying out dispersion treatment by ultrasound and the like as necessary. Washing by this series of procedures consisting of precipitation by centrifugation, removal of supernatant and addition of liquid is carried out as many times as necessary to prepare a dispersion containing a prescribed concentration of microparticles which have undergone antibody adsorption and blocking. Protein, surfactant and sugar such as sucrose or trehalose and the like are added to the dispersion as necessary, a certain amount of the resulting solution is coated onto conjugate pad made of glass fiber followed by drying to prepare a portion containing the detection reagent. In addition, buffers, surfactants, proteins, reagents that trap contaminants present in the specimen sample, preservatives, antibacterial agents, antioxidants or hygroscopic agents and the like are coated onto regenerated cellulose continuous long fiber nonwoven fabric as necessary followed by drying to prepare a sample pad. Moreover, a porous nitrocellulose membrane having antibody immobilized thereon at prescribed locations and an absorbent pad made of cellulose filter paper for absorbing the specimen are prepared. These components are immobilized on a sheet referred to as a packing sheet having an adhesive site which is then cut to a prescribed size to prepare an immunochromatographic diagnostic kit.

EXAMPLES

Although the following provides a more detailed explanation of the present invention through examples thereof, the present invention is not limited to only these examples. In addition, all procedures were carried out at a temperature of 23° C. and relative humidity of 55% RH unless specifically indicated otherwise.

First, an explanation is provided of the methods used to measure various physical properties.

[Microparticle Average Particle Diameter]

The Model UPA-EX150 Nanotrac Particle Size Analyzer (dynamic light scattering system) manufactured by Nikkiso Co., Ltd. was used for the apparatus. A sample containing 0.01% by weight of microparticles and 99.99% by weight of water was used for the measurement sample. Measuring conditions consisted of 30 integration cycles, measuring time of 30 seconds per measurement, use of the volume average of particle diameter distribution, and taking the median thereof to be average particle diameter.

[Microparticle Coloring Intensity]

An apparatus having the Model ISV-722 Integrating Sphere Unit manufactured by Jasco Corp. attached to the JASCO Model V-650 UV-Visible/Near Infrared Spectrophotometer manufactured by same manufacturer was used for the apparatus. A sample containing 0.01% by weight of microparticles and 99.99% by weight of water was used for the measurement sample and the sample was measured by placing in a quartz cell having an optical path length of 10 mm. The maximum value (ABS) of the resulting absorbance peaks within the visible light range of 400 nm to 800 nm was taken to be the coloring intensity.

[Microparticle L/D Ratio (Sphericity)]

The Model JSM-6700 Scanning Electron Microscope manufactured by JEOL Ltd. was used for the apparatus. A sample containing 0.01% by weight of microparticles and 99.99% by weight of water was dropped onto a mica plate, the microparticles were allowed to be adsorbed onto the mica plate by allowing ten seconds to elapse and excess liquid was absorbed with a Kimwipe followed by drying. The resulting mica plate was coated with platina to prepare a sample for electron microscope measurement. Observation was carried out at an acceleration voltage of 1.6 kV and measuring magnification factor of 50,000×, the required number of images were photographed so that the number of microparticles images was 100 or more, and major axis (L) and minor axis (D) were measured for each microparticle followed by calculating the average value of the L/D ratio for 100 microparticles.

[Identification of Spacer Structures]

A nuclear magnetic resonance system (Avance II 400) manufactured by Bruker Corp. was used for the apparatus. 0.1 mL of a 1.0 M aqueous sodium hydroxide solution (Wako Pure Chemical Industries, Ltd., 72082100) or 10.0 mL of a 1.0 M aqueous hydrochloric acid solution (Wako Pure Chemical Industries, Ltd., 080-10035) were added to a 1.0% by weight dispersion of microparticles introduced with spacers followed by heating and stirring for 5 hours at 60° C. Subsequently, the supernatant was collected by centrifugation to obtain a solution in which the spacers had been dissolved or dispersed from the microparticles. This solution was diluted with an optimal heavy solvent and the structures were identified from the spectrum obtained by NMR using the nuclear magnetic resonance system.

[Amount of Carboxyl Groups Introduced]

The Model FP-8300 Spectrofluorometer manufactured by Jasco Corp. was used for the apparatus. A reagent that emits light only in the case of having reacted with carboxyl groups was bound to the microparticles and the introduced amount of carboxyl groups was measured from the fluorescence intensity thereof. The following indicates a measurement example. 0.1 mL of a 1.0% by weight dispersion of microparticles desired to be measured for the introduced amount of carboxyl groups, 4.0 mL of a 2.3 mM ethanol solution of fluorescent reagent ADAM (KAK Corp., FK-101) and 3.9 mL of ethanol (Kanto Chemical Co., Inc., 14033-70) were placed in a container and allowed to react for 5 minutes at 60° C. Subsequently, 2.0 mL of ethanol were added to 10.0 µL of the resulting reaction solution and irradiated with excitation light at 365 nm with the FP-8300 to measure fluorescence intensity at 410 nm. Octanoic acid (Tokyo Chemical Industry Co., Ltd., 00027) was used for the calibration curve.

[Amount of Residual Reactive Amino Groups]

The Model FP-8300 Spectrofluorometer manufactured by Jasco Corp. was used for the apparatus. A reagent that emits light only in the case of having reacted with amino groups was bound to the microparticles and the introduced amount of amino groups was measured from the fluorescence intensity thereof. The following indicates a measurement example. 0.1 mL of a 1.0% by weight dispersion of microparticles desired to be measured for the introduced amount of amino groups, 4.0 mL of a 2.5 mM ethanol solution of fluorescent reagent NBD-F (Dojin Chemical Co., Ltd.) and 3.9 mL of ethanol (Kanto Chemical Co., Inc., 14033-70) were placed in a container and allowed to react for 60 minutes at 30° C. Subsequently, 2.0 mL of ethanol were added to 10.0 µL of the resulting reaction solution and irradiated with excitation light at 480 nm with the FP-8300 to measure fluorescence intensity at 530 nm. Octylamine (Tokyo Chemical Industry Co., Ltd., 00045) was used for the calibration curve.

[Microparticle Degree of Hydrophilization]

A microparticle dispersion was adjusted to a concentration of 1% (wt/vol) and used as a sample solution. After stirring, 0.5 mL of the sample solution was transferred to a glass NMR tube having an outer diameter of 10 mm and placed in a pulsed NMR system set to 30° C. The Minispec mq20 system manufactured by Bruker Corporation was used for the pulsed NMR system. The sample solution was measured after setting each of the parameters as indicated below.

Observed nucleus: $^1$H

Measured relaxation time: Transverse relaxation time T2 (ms)

Measurement mode: CPMG method

Integration cycles: 32

Recycle delay: 10 (s)

90°-180° pulse separation (τ): 2 (ms)

The resulting magnetization decay curves (curves indicating time-based changes in magnetization intensity) were fit to the following equation (1) according to the least squares method using the exponential approximation function of Microsoft Excel.

$$M(t)=M_0 \cdot \exp(-t/T2) \quad \text{(Equation 1)}$$

(wherein, M(t) represents signal strength at a certain time t, $M_0$ represents the initial value of signal strength, and T2 represents relaxation time).

Next, as shown in FIG. 1, a graph was prepared by plotting the rate of change in relaxation time (Rsp value) on the vertical axis and the total surface area (TSA value) of the microparticles on the horizontal axis. An approximation curve was prepared according to the least squares method, the slope thereof was defined as the degree of hydrophilization, and the degree of hydrophilization of the microparticles was compared. The methods used to calculate Rsp value and TSA value are as indicated below.

Calculation of Rsp Value:

$$Rsp \text{ value} = Rav \div Rb - 1$$

(wherein Rav represents an average relaxation time constant (reciprocal of relaxation time of sample) and Rb represents a relaxation time constant of bulk microparticles (reciprocal of relaxation time of water blank).

Calculation of TSA Value (m²):

$$TSA \text{ value} = SA \times V \times \psi_p \times \rho$$

(wherein, SA represents microparticle specific surface area $(m^2/g) = 6 \div \rho \times d$), where p represents microparticle density (g/cm³) (microparticle density: 1.4 g/cm³, latex particle density: 1.0 g/cm³, colloidal gold particle density: 19.3 g/cm³), d represents microparticle diameter (μm), V represents NMR tube volume of the portion irradiated with radio waves (cm³) (≈ amount of sample), $\psi_p$ represents microparticle volume ratio, where microparticle volume (i)=microparticle concentration (wt %)÷100÷microparticle density, water volume (ii)=(1−microparticle volume (i))÷water density (0.997 g/cm³) and ψp (microparticle volume ratio) =microparticle volume (i)÷water volume (ii), with ρ having the same meaning as previously described).

[Adsorbed Amount of Protein]

The JASCO Model V-650 UV-Visible/Near Infrared Spectrophotometer manufactured by Jasco Corp. was used for the apparatus. The following indicates the method for calculating the adsorbed amount of protein using the example of bovine serum albumin (BSA, Sigma-Aldrich Corp., A7906). 30.0 μL of a 1.0% by weight dispersion of microparticles for which the adsorbed amount of protein is desired to be measured, 270.0 μL of phosphate buffer having a pH of 5.0 and concentration of 100 mM (Kishida Chemical Co., Ltd.) and 3.0 μL of 1.0% by weight BSA solution were allowed to react for 2 hours at 37° C. after which the supernatant was collected by centrifugation. This supernatant was reacted with a commercially available BCA reagent (Wako Pure Chemical Industries, Ltd., 297-73101) and absorbance at 562 nm was measured with the V-650 followed by calculating the amount of BSA in the supernatant. Subsequently, the amount of BSA in the supernatant was subtracted from the loaded amount of BSA followed by dividing by the amount of microparticles used to calculate the degree to which BSA was adsorbed thereto.

[Method for Binding Hydrophilized Cellulose Microparticles Introduced with Carboxyl Groups and Antibody]

2-morpholinoethane sulfonic acid (MES) buffer having a pH of 6.0 and concentration of 100 mM was prepared using MES (Tokyo Chemical Industry Co., Ltd., M0606), caustic soda and water. 63.0 μL of the resulting MES buffer, 7.0 μL of a 1.0% by weight dispersion of carboxyl group-introduced hydrophilized colored cellulose microparticles, 3.5 μL of a 1.0% by weight solution of 1-ethyl-3-(3-dimethylaminopropyl)carboximide hydrochloride (EDC, Tokyo Chemical Industry Co., Ltd., D1601) and 7.0 μL of a 1.0% by weight solution of N-hydroxysuccinimide (NHS, Tokyo Chemical Industry Co., Ltd., B0249) were placed in a container and stirred for 15 minutes at room temperature. Subsequently, the supernatant was discarded by centrifugation to remove unreacted EDC and NHS. 70.0 μL of MES buffer were then placed in the container to suspend the microparticles followed by adding anti-hCG antibody (Fitzgerald, #5014) to the carboxyl group-introduced hydrophilized colored cellulose microparticles to a Spitz tube to a concentration of 10.0% by weight followed by reacting for 2 hours at 37° C. Subsequently, 840.0 μL of a protein solution (100 mM, borate buffer, pH=8.5) containing 1.0% by weight casein (Wako Pure Chemical Industries, Ltd., 030-01505) were added to a Spitz tube and allowed to stand undisturbed for 1 hour in a dryer at 37° C. One hour later, centrifugation was carried out at 14,000 g for 30 minutes using a centrifuge (Kubota Corp., 6200) and centrifuge rotor (Kubota Corp., AF-5008C), and after the antibody-bound carboxyl group-introduced hydrophilized colored cellulose microparticles had precipitated, the supernatant was discarded. Next, 840.0 μL of borate buffer (50 mM, pH=10.0) were added to the Spitz tube followed by treating for 10 seconds with an ultrasonic homogenizer (SMT Co., Ltd. UH-50) to disperse the antibody-bound carboxyl group-introduced hydrophilized colored cellulose microparticles. After adequately dispersing, centrifugation was carried out at 14000 g for 20 minutes followed by discarding the supernatant. Borate buffer (50 mM, pH=10.0) was then added so that the concentration of antibody-bound carboxyl group-introduced hydrophilized colored cellulose microparticles was 0.04% by weight followed by adequately dispersing with the ultrasonic homogenizer. Antibody-bound carboxyl group-introduced hydrophilized colored cellulose microparticles (to be referred to as the "detection reagent") were obtained according to the method described above.

[Impregnation of Detection Reagent into Conjugate Pad and Drying]

A polyethylene phthalate conjugate pad (Ah Corp., 6615) was immersed in 0.05% by weight Tween-20 (Sigma-Aldrich Corp., T2700) and dried for 60 minutes at 50° C. after removing excess liquid. Next, the conjugate pad was cut to a shape having a height of 10 mm and length of 300 mm. Next, the detection reagent was uniformly coated onto the conjugate pad at 272 μL/800 mm² using a micropipette followed by drying for 30 minutes at 37° C.

[Pretreatment of Sample Pad]

A regenerated cellulose continuous long fiber nonwoven fabric was impregnated with a large excess PBS buffer (66 mM, pH 7.4) containing 2.0% by weight BSA (Sigma-Aldrich Corp., A7906) and 2.0% by weight Tween-20 and dried for 60 minutes at 50° C. after removing excess liquid. Next, the nonwoven fabric was cut to a shape having a height of 20 mm and length of 300 mm.

[Preparation of Capture Antibody-Coated Membrane]

A nitrocellulose membrane (Millipore Corp., SHF0900425) was cut to a shape having a width of 25 mm and length of 300 mm. A PBS solution (66 mM, pH 7.4) containing 0.1% by weight hCG-β mouse antibody (Medix Biochemical Inc., 6601) was coated onto a portion having a height of 12 mm at a ratio of 0.1 μL/mm using a liquid coating system (Musashi Engineering Inc., 300DS). Next, the membrane was dried for 30 minutes at 37° C.

[Preparation of Immunochromatographic Diagnostic Kit]

The capture antibody-coated membrane obtained in the manner described above, an absorbent pad (Millipore Corp., C083), the conjugate pad containing the detection reagent and the sample pad were adhered to a backing card (Adhesives Research, Inc., AR9020). Next, the card was cut to a width of 5 mm with a cutter to obtain an immunochromatographic diagnostic kit having width of 5 mm and length of 60 mm.

[Evaluation of False Positives of Immunochromatographic Diagnostic Kit]

Figure 2:
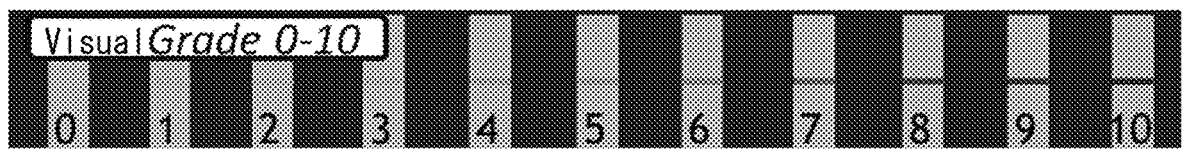
FIG. 2 is a photograph indicating coloring intensity (visual grade on an 11-grade scale from grade 0 to 10) of a test line (TL) during an assay with an immunochromatographic diagnostic kit.

False positives were measured using urine obtained from 100 non-pregnant women. 15 minutes later, the coloring intensity of the test line (TL) was visually evaluated to one of eleven grades ranging from 0 to 10. As shown in FIG. 2, a higher value for the visual grade represents a darker color on the line of the TL and a grade of 0 indicates that the line is not visible. This measurement was carried out five times and the specimen was judged to not be a false positive if the average value of the resulting values yielded a visual grade of 0. The number of specimens that demonstrated a false positive was counted among 100 specimens and the result of dividing that number by 100 was taken to be incidence of false positives. In addition, the visual grades were recorded for those specimens that were judged to be false positives.

[Diagnosis Time of Immunochromatographic Diagnostic Kit]

An immunochromatographic diagnostic kit cut to a width of 5 mm was placed in a plastic housing. The resulting diagnostic kit placed in the housing was visually evaluated to one of eleven grades ranging from 0 to 10. Anti-hCG-β mouse antibody was used for the test target substance. The aforementioned hCG antibody was diluted with 66 mM, pH 7.4 phosphate buffer containing 1.0% by weight BSA (to be referred to as "PBS") to prepare a positive specimen containing the aforementioned hCG antibody at 10.0 mIU/mL. 120.0 μL of this positive specimen were dropped onto the sample dropping portion of the diagnostic kit followed by measuring time-based changes in the TL by making visual measurements every 20 seconds. The amount of time until the coloring intensity of the resulting TL reached 1.0 or higher was measured with an Immunochromato-Reader. Here, the reason for measuring to a value of 1.0 or higher is that, although there are individual differences, the presence of the TL can be confirmed visually if the value is 1.0 or higher. This measurement was carried out five times and the average time was taken to be the diagnosis time.

[Detection Limit of Immunochromatographic Diagnostic Kit]

An immunochromatographic diagnostic kit cut to a width of 5 mm was placed in a plastic housing. The resulting diagnostic kit placed in the housing was visually evaluated to one of eleven grades ranging from 0 to 10. Human chorionic gonadotropin (to be referred to as "hCG") was used for the test target substance. The hCG was diluted with 66 mM, pH 7.4 phosphate buffer containing 1.0% by weight BSA (to be referred to as "PBS") to prepare positive specimens having incrementally decreasing concentrations of the aforementioned hCG consisting of 1.600 mIU/mL, 0.800 mIU/mL, 0.400 mIU/mL, 0.200 mIU/mL, 0.100 mIU/mL, 0.050 mIU/mL, 0.025 mIU/mL, 0.013 mIU/mL, 0.007 mIU/mL, and 0.0025 mIU/mL. 120.0 μL of this positive specimen were dropped onto the sample dropping portion of the diagnostic kit followed by visually evaluated coloring intensity of the TL 15 minutes later. This measurement was carried out five times at each concentration, the specimen was judged to be positive in the case the average value of the resulting values was 1.0 or more, and the specimen was judged to be below the detection limit in the case the average value was less than 1.0. The lower limit of hCG concentration at which this positive judgment was obtained was taken to be the detection limit.

Example 1

A cuprammonium cellulose solution was prepared using a conventionally known method having a cellulose concentration of 0.37% by weight, copper concentration of 0.13% by weight and ammonia concentration of 1.00% by weight. A coagulation liquid was further prepared having a tetrahydrofuran concentration of 89.00% by weight and water concentration of 11.00% by weight.

500 g of the prepared cuprammonium cellulose solution were added while gently stirring 5000 g of the coagulation liquid using a magnetic stirrer. After continuing to stir for about 5 seconds, 1000 g of 10% by weight sulfuric acid were added to neutralize the solution and regenerate cellulose to obtain 6500 g of a slurry containing cellulose microparticles.

The resulting slurry was centrifuged for 10 minutes at a speed of 10000 rpm. After removing the precipitate by decantation, deionized water was injected followed by stirring and re-centrifugation. This procedure was repeated several times until the pH reached 6.0 to 7.0, after which dispersion treatment was carried out with a high-pressure homogenizer to obtain 150 g of a cellulose microparticle suspension. As a result of measuring the average particle diameter of the resulting cellulose microparticles, the average particle diameter was 261 nm.

Next, the cellulose microparticles prepared in the manner described above were dyed. 30 g of sodium sulfate and 1.00 g of reactive dye (Dystar Japan, Ltd., Levafix Red CA GR®) were added to 100 g of the cellulose microparticle dispersion adjusted to a microparticle concentration of 1.00% by weight followed by heating to 60° C. using a thermostatic chamber while stirring. After heating to 60° C., 4 g of sodium carbonate were added followed by dyeing for 2 hours. The resulting coloring microparticles were then subjected to a total of three cycles of a series of procedures, with one cycle consisting of washing with a 5% aqueous sodium hydroxide solution, recovering by centrifugation, washing with pure water and finally recovering by centrifugation, to obtain colored cellulose microparticles.

Next, a surface hydrophilization reaction was carried out on the colored cellulose microparticles prepared in the manner described above. 10.0 mL of N-2-(aminoethyl)-3-aminopropyltrimethoxysilane (Tokyo Chemical Industry Co., Ltd., A0774) as hydrophilizing agent and 50.0 mL of N,N-dimethylformamide (Tokyo Chemical Industry Co., Ltd., D0939) were added to 10.0 mL of the colored cellulose microparticles adjusted to 10.0% by weight followed by heating to 50° C. using a thermostatic chamber while stirring and reacting for 4 hours. Following the reaction, the microparticles were recovered by centrifugation and washed with pure water followed by recovering by centrifugation. The aforementioned washing procedure was repeated until the pH reached 11.00 to obtain hydrophilized colored cellulose microparticles. Degree of hydrophilization and other particle properties are shown in the following Table 1.

Next, a reaction was carried out for introducing carboxyl groups into the hydrophilized colored cellulose microparticles prepared in the manner described above. 6.0 g of 6-bromohexanoic acid (Tokyo Chemical Industry Co., Ltd., B1290) as reactant, 50.0 mL of N,N-dimethylformamide (Tokyo Chemical Industry Co., Ltd., D0939) and 0.1 g of sodium carbonate (Kishida Chemical Co., Ltd., 000-71245) were added to 10.0 mL of a hydrophilized colored cellulose microparticle suspension adjusted to 5.0% by weight followed by heating to 50° C. using a thermostatic chamber while stirring and reacting for 6 hours. Following the reaction, the microparticles were recovered by centrifugation and washed by centrifuging three times with 2-propanol (Tokyo Chemical Industry Co., Ltd., 10277) followed by washing by centrifuging three times with pure water to obtain carboxyl group-introduced surface-hydrophilized colored cellulose microparticles. Since the resulting microparticles were in sodium carboxylate form, 15.0 mL of a 0.1 M HCl solution (Wako Pure Chemical Industries, Ltd., 083-01115) and 35.0 mL of pure water were added and reacted for 2 hours at room temperature. Subsequently, the microparticles were recovered by centrifugation and washed with pure water followed by recovering by centrifugation. Washing was carried out until the pH reached 4.0 or higher to obtain a carboxyl group-introduced hydrophilized colored cellulose microparticle dispersion. Properties such as the introduced amount of carboxyl groups, and immunochromatographic performance when these microparticles were used as coloring particles, are shown in the following Table 1. Adsorption of protein was able to be reduced considerably due to the effects of the hydrophilic layer and spacers. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 2

Carboxyl group-introduced hydrophilized colored cellulose microparticles were prepared using the same method as Example 1 with the exception of changing the amount of sodium carbonate used in the carboxyl group introduction reaction to 9.9 g. The properties of the microparticles and immunochromatographic performance when used as colored microparticles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 3

Carboxyl group-introduced hydrophilized colored cellulose microparticles were prepared using the same method as Example 1 with the exception of changing the amount of sodium carbonate used in the carboxyl group introduction reaction to 29.7 g. The properties of the microparticles and immunochromatographic performance when used as coloring particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 4

Carboxyl group-introduced hydrophilized colored cellulose microparticles were prepared using the same method as Example 1 with the exception of carrying out the dyeing reaction for 5 cycles and changing the amount of sodium carbonate used in the carboxyl group introduction reaction to 9.9 g. The properties of the microparticles and immunochromatographic performance when used as coloring particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 5

Carboxyl group-introduced hydrophilized colored cellulose microparticles were prepared using the same method as Example 1 with the exception of changing the reactant to 7.2 g of 11-bromoundecanoic acid (Tokyo Chemical Industry Co., Ltd., B0389) and the amount of sodium carbonate to 9.9 g in the carboxyl group introduction reaction. The properties of the microparticles and immunochromatographic performance when used as colored particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 6

Carboxyl group-introduced hydrophilized colored cellulose microparticles were prepared using the same method as Example 1 with the exception of changing the reactant to 10.0 g of eicosanedioic acid (Tokyo Chemical Industry Co., Ltd., E0320) and the amount of sodium carbonate to 9.9 g in the carboxyl group introduction reaction. The properties of the microparticles and immunochromatographic performance when used as colored particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 7

Carboxyl group-introduced hydrophilized colored cellulose microparticles were prepared using the same method as Example 1 with the exception of changing the reactant to 6.5 g of terephthalic acid (Tokyo Chemical Industry Co., Ltd., T0166) and the amount of sodium carbonate to 9.9 g in the carboxyl group introduction reaction. The properties of the microparticles and immunochromatographic performance when used as colored particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 8

Carboxyl group-introduced hydrophilized colored cellulose microparticles were prepared using the same method as Example 1 with the exception of changing the coagulation liquid to that having an ethyl acetate (Tokyo Chemical Industry Co., Ltd., Q0040) concentration of 94.0% by weight and water concentration of 6.0% by weight in the cellulose microparticle coagulation reaction and changing the amount of sodium carbonate to 9.9 g in the carboxyl group introduction reaction. The properties of the microparticles and immunochromatographic performance when used as coloring particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 9

Carboxyl group-introduced hydrophilized colored cellulose microparticles were prepared using the same method as Example 1 with the exception of changing the coagulation liquid to that having an acetone concentration of 27.0% by weight, water concentration of 0.2% by weight and ammonia concentration of 72.8% by weight in the cellulose microparticle coagulation reaction and changing the amount of sodium carbonate to 9.90 g in the carboxyl group introduction reaction. The properties of the microparticles and immunochromatographic performance when used as coloring particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 10

Carboxyl group-introduced hydrophilized colored cellulose microparticles were prepared using the same method as Example 1 with the exception of changing the amount of sodium carbonate to 9.9 g and the reactant to 4.2 g of 3-bromopropionic acid (Tokyo Chemical Industry Co., Ltd., B0645) in the carboxyl group introduction reaction. The properties of the microparticles and immunochromatographic performance when used as coloring particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 11

Carboxyl group-introduced hydrophilized colored cellulose microparticles were prepared using the same method as Example 1 with the exception of changing the hydrophilizing agent to a mixture of 10.0 mL of N-2-(aminoethyl)-3-aminopropyltrimethoxysilane (Tokyo Chemical Industry Co., Ltd., A0774) and 10.0 mL of polyethylene glycol silane (Mw 2000, Creative PEGWorks, PLS-2012) in the surface hydrophilization reaction, and changing the reactant to 7.2 g of 11-bromoundecanoic acid in the carboxyl group introduction reaction. The properties of the microparticles and immunochromatographic performance when used as coloring particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 12

Carboxyl group-introduced hydrophilized colored cellulose microparticles were prepared using the same method as Example 1 with the exception of changing the hydrophilizing agent to 10.0 mL of amino-PEG12-propionic acid (Sigma-Aldrich Corp., JKA12006) in the surface hydrophilization reaction, and changing the reactant to 7.2 g of 11-bromoundecanoic acid and the amount of sodium carbonate to 9.9 g in the carboxyl group introduction reaction. The properties of the microparticles and immunochromatographic performance when used as coloring particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 13

Carboxyl group-introduced hydrophilized colored cellulose microparticles were prepared using the same method as Example 1 with the exception of changing the reactant to 11.0 g of $Br-(CH_2)_{30}-COOH$ and the amount of sodium carbonate to 9.9 g in the carboxyl group introduction reaction. The properties of the microparticles and immunochromatographic performance when used as coloring particles are shown in the following Table 1. Adsorption of protein was able to be reduced considerably as a result of hydrophilizing with a hydrophilic layer and introducing hydrophobic spacers and carboxyl groups in the same manner as Example 1. As a result, the incidence of false positives was 0%. High detection sensitivity was maintained since antibodies were adequately immobilized on the surface of the microparticles due to the large number of carboxyl groups. In addition, diagnosis time was able to be shortened since the microparticles were able to migrate rapidly without being adsorbed to the membrane due to the effect of the hydrophilic layer.

Example 14

Carboxyl group-introduced hydrophilized colored cellulose microparticles were prepared using the same method as Example 1 with the exception of changing the amount of sodium carbonate to 0.01 g in the carboxyl group introduction reaction. The properties of the microparticles and immunochromatographic performance when used as coloring particles are shown in the following Table 1. Adsorption of protein was able to be reduced in comparison with the following Comparative Example 1 and the like due to the effects of the hydrophilic layer and hydrophilic spacers and a false positive reduction effect was observed.

Example 15

Carboxyl group-introduced hydrophilized colored cellulose microparticles were prepared using the same method as Example 1 with the exception of changing the reactant in the carboxyl group introduction reaction to 16.4 g of poly(ethylene glycol) bis(carboxymethyl) ether (Mw 600, Creative PEGWorks, PSB-362). The properties of the microparticles and immunochromatographic performance when used as coloring particles are shown in the following Table 1. Adsorption of protein was able to be reduced slightly in comparison with the following Comparative Example 1 and the like due to the effects of the hydrophilic layer and hydrophilic spacers and a false positive reduction effect was observed.

Example 16

Carboxyl group-introduced hydrophilized colored cellulose microparticles were prepared using the same method as Example 1 with the exception of changing the amount of hydrophilizing agent to 40.0 mL in the surface hydrophilization reaction and changing the reactant to 7.2 g of 11-bromoundeanoic acid in the carboxyl group introduction reaction. The properties of the microparticles and immunochromatographic performance when used as coloring particles are shown in the following Table 1. Adsorption of protein was able to be reduced in comparison with the following Comparative Example 1 and the like due to the effects of the hydrophilic layer and hydrophilic spacers and a false positive reduction effect was observed.

Example 17

Carboxyl group-introduced hydrophilized colored cellulose microparticles were prepared using the same method as Example 1 with the exception of changing the amount of hydrophilizing agent to 8.0 mL in the surface hydrophilization reaction, and changing the reactant to 16.4 g of poly(ethylene glycol) bis(carboxymethyl) ether (Mw 600, Creative PEGWorks, PSB-362) and the amount of sodium carbonate to 0.01 g in the carboxyl group introduction reaction. The properties of the microparticles and immunochromatographic performance when used as coloring particles are shown in the following Table 1. Adsorption of protein was improved slightly in comparison with the following Comparative Example 1. Adsorption of protein was able to be reduced slightly in comparison with the following Comparative Example 1 and the like and a false positive reduction effect was observed.

Example 18

Carboxyl group-introduced hydrophilized colored cellulose microparticles were prepared using the same method as Example 1 with the exception of changing the amount of hydrophilizing agent to 40.0 mL in the surface hydrophilization reaction, and changing the reactant to 16.4 g of poly(ethylene glycol) bis(carboxymethyl) ether (Mw 600, Creative PEGWorks, PSB-362) and the amount of sodium carbonate to 9.9 g in the carboxyl group introduction reaction. The properties of the microparticles and immunochromatographic performance when used as coloring particles are shown in the following Table 1. Adsorption of protein was improved slightly in comparison with the following Comparative Example 1. As a result, a false positive reduction effect was observed, although only slightly.

Example 19

Carboxyl group-introduced hydrophilized colored cellulose microparticles were prepared using the same method as Example 1 with the exception of changing the reactant to 7.2 g of 11-bromoundecanoic acid and the amount of sodium carbonate to 0.01 g. The properties of the microparticles and immunochromatographic performance when used as coloring particles are shown in the following Table 1. Adsorption of protein decreased in comparison with the following Comparative Example 1 due to the effects of the hydrophilic layer and hydrophilic spacers. As a result, a false positive reduction effect was observed.

Example 20

Carboxyl group-introduced hydrophilized colored cellulose microparticles were prepared using the same method as Example 1 with the exception of changing the reactant to 16.4 g of poly(ethylene glycol) bis(carboxymethyl) ether (Mw 600, Creative PEGWorks, PSB-362) and the amount of sodium carbonate to 0.01 g in the carboxyl group introduction reaction. The properties of the microparticles and immunochromatographic performance when used as coloring particles are shown in the following Table 1. Adsorption of protein was improved slightly in comparison with the following Comparative Example 1. As a result, a false positive reduction effect was observed.

Example 21

Carboxyl group-introduced hydrophilized colored cellulose microparticles were prepared using the same method as Example 1 with the exception of changing the reactant to 65.6 g of poly(ethylene glycol) bis(carboxymethyl) ether (Mw 5000, Creative PEGWorks, PSB-366) and the amount of sodium carbonate to 9.9 g in the carboxyl group introduction reaction. The properties of the microparticles and immunochromatographic performance when used as coloring particles are shown in the following Table 1. Although the spacers were PEG, an excluded volume effect was demonstrated due to the long length thereof and the amount of adsorbed protein being zero. As a result, a false positive reduction effect was observed.

In the microparticles prepared in Examples 1 to 21, coloring intensity of the microparticles at the stage prior to binding with antibody did not decrease due to introduction of reactive groups perhaps due to the hydrophilic layer having functioned as a protective layer.

Comparative Example 1

Colored cellulose microparticles were prepared using the same method as Example 1 with the exception of not carrying out the surface hydrophilization reaction and carboxyl group introduction reaction. The properties of the microparticles and immunochromatographic performance when used as coloring particles are shown in the following Table 2. A large amount of protein was thought to have easily been adsorbed onto the surface of the microparticles due to the surface of the microparticles being hydrophobic. As a result, non-specific adsorption occurred and the incidence of false positives was 3%.

Comparative Example 2

Carboxyl group-introduced colored cellulose microparticles in which the spacers were $(CH_2)_{16}$ were prepared according to the method described in PTL4. The properties of the microparticles and immunochromatographic performance when used as coloring particles are shown in the following Table 2. Although sensitivity improved dramatically in comparison with PTL4 since a different amount of antibody was used from that used in PTL4, since the surface of the microparticles was hydrophobic, a large amount of protein was adsorbed onto the surface of the microparticles, thereby causing non-specific adsorption and resulting in an incidence of false positives of 3%.

Comparative Example 3

Carboxyl group-introduced colored cellulose microparticles were prepared using the same method as Example 1 with the exception of not carrying out the surface hydrophilization reaction. The properties of the microparticles and immunochromatographic performance when used as coloring particles are shown in the following Table 2. Adsorption of protein was improved slightly in comparison with Comparative Example 1 or 2 perhaps due to having introduced a slightly large amount of carboxyl groups. However, the degree of hydrophilization was low and protein ended up being adsorbed due to the absence of a hydrophilic layer, and there was hardly any false positive reduction effect.

Comparative Example 4

Amino groups were introduced onto the surface of microparticles using the method described in PTL4 without carrying out surface hydrophilization. Subsequently, carboxyl group-introduced colored cellulose microparticles were prepared using the same method as Example 1. The properties of the microparticles and immunochromatographic performance when used as coloring particles are shown in the following Table 2. A protein adsorption reduction effect was not observed due to the absence of a hydrophilic layer in addition to the large amount of residual reactive amino groups. As a result, a false positive reduction effect was also not observed.

Comparative Example 5

Carboxyl group-introduced colored cellulose microparticles were prepared using the same method as Example 1 with the exception of not carrying out the surface hydrophilization reaction and changing the reactant in the carboxyl group introduction reaction to 16.40 g of poly(ethylene glycol) bis(carboxymethyl) ether (Mw600, Creative PEGWorks, PBS-362). The properties of the microparticles and immunochromatographic performance when used as coloring particles are shown in the following Table 2. In addition to protein being adsorbed due to electrical interaction between the microparticle surface and spacers as a result of the absence of a hydrophilic layer and the use of PEG for the spacers, inadequate hydrophilicity of the microparticle surface also resulted in adsorption of protein, and an effect of reducing the adsorbed amount was not observed. As a result, a false positive reduction effect was also not observed.

Comparative Example 6

Amino groups were introduced into microparticles using the same method as Comparative Example 4 without carrying out surface hydrophilization. Subsequently, carboxyl group-introduced colored cellulose microparticles were prepared using the same method as Example 1 with the exception of changing the reactant to 11-bromoundecanoic acid and the amount of sodium carbonate to 0.01 g in the carboxyl group introduction reaction. The properties of the microparticles and immunochromatographic performance when used as coloring particles are shown in the following Table 2. Due to the absence of a hydrophilic layer and the large amount of residual reactive amino groups, hydrophilicity of the microparticle surface was inadequate and a protein adsorption reduction effect was not observed. As a result, a false positive reduction effect was also not observed.

Comparative Example 7

Amino groups were introduced into microparticles using the same method as Comparative Example 4 without carrying out surface hydrophilization. Subsequently, carboxyl group-introduced colored cellulose microparticles were prepared using the same method as Example 1 with the exception of changing the reactant to 16.4 g of poly(ethylene glycol) bis(carboxymethyl) ether (Mw600, Creative PEGWorks, PSB-362) in the carboxyl group introduction reaction. The properties of the microparticles and immunochromatographic performance when used as coloring particles are shown in the following Table 2. Due to the absence of a hydrophilic layer and the large amount of residual reactive amino groups, a protein adsorption reduction effect was not observed since hydrophilicity of the microparticle surface was inadequate and PEG was used for the spacers. As a result, a false positive reduction effect was also not observed.

Comparative Example 8

Amino groups were introduced into microparticles using the same method as Comparative Example 4 without carrying out surface hydrophilization. Subsequently, carboxyl group-introduced colored cellulose microparticles were prepared using the same method as Example 1 with the exception of changing the reactant to 16.4 g of poly(ethylene glycol) bis(carboxymethyl) ether (Mw600, Creative PEGWorks, PSB-362) and the amount of sodium carbonate to 0.01 g in the carboxyl group introduction reaction. The properties of the microparticles and immunochromatographic performance when used as coloring particles are shown in the following Table 2. Due to the absence of a hydrophilic layer and the large amount of residual reactive amino groups, a protein adsorption reduction effect was not observed since hydrophilicity of the microparticle surface was inadequate and PEG was used for the spacers. As a result, a false positive reduction effect was also not observed.

Comparative Example 9

Carboxyl group-introduced hydrophilized colored cellulose microparticles were prepared using the same method as Example 1 with the exception of changing the number of cycles of the dyeing reaction to one cycle. The properties of the microparticles and immunochromatographic performance when used as coloring particles are shown in the following Table 2. Detection sensitivity was inferior to the examples due to the low coloring intensity and diagnosis time was longer accompanying this.

Comparative Example 10

Carboxyl group-introduced hydrophilized colored cellulose microparticles were prepared using the same method as Example 1 with the exception of changing the coagulation liquid to 50.00% by weight of dimethylsulfoxide (Tokyo Chemical Industry Co., Ltd., D0798) and 50.00% by weight water. The properties of the microparticles and immunochromatographic performance when used as coloring particles are shown in the following Table 2. Detection sensitivity was inferior to the examples due to the small particle diameter and diagnosis time was longer accompanying this.

Comparative Example 11

Carboxyl group-introduced hydrophilized colored cellulose microparticles were prepared using the same method as Example 1 with the exception of changing the amount of hydrophilizing agent in the surface hydrophilization reaction to 1.0 mL. The properties of the microparticles and immunochromatographic performance when used as coloring particles are shown in the following Table 2. Coloring intensity of the microparticles decreased considerably during the carboxyl group introduction reaction due to a lack of a hydrophilic layer.

Comparative Example 12

Carboxyl group-introduced hydrophilized colored cellulose microparticles were prepared using the same method as Example 1 with the exception of changing the coagulation liquid to a tetrahydrofuran concentration of 97.0% by weight and water concentration of 3.0% by weight in the cellulose microparticle coagulation reaction, and changing the amount of sodium carbonate to 9.9 g and the reactant to 7.2 g of 11-bromoundecanoic acid in the carboxyl group introduction reaction. The properties of the microparticles and immunochromatographic performance when used as coloring particles are shown in the following Table 2. The microparticles were unable to move through the membrane due to the diameter of the microparticles being excessively large.

Comparative Example 13

2000 Da PEG linkers consisting of carboxyl group-modified gold nanoparticles having a particle diameter of 50 nm and introduced with carboxyl groups (CTD Inc.) were used as coloring particles and evaluated for immunochromatographic performance. The results are shown in the following Table 2. Time was required for the microparticles to move through the membrane due to the hydrophobic surface thereof and coloring time was slow. In addition, since the surface of the microparticles was hydrophobic, proteins were easily adsorbed to the microparticle surface and false positives occurred easily.

Comparative Example 14

Latex particles having a particle diameter of 470 nm, coloring intensity of 0.5 and introduced with carboxyl groups (Bangs Laboratories, Inc.) were used as coloring particles and evaluated for immunochromatographic performance. The results are shown in the following Table 2. Since the microparticle surface was hydrophobic, protein easily adsorbed to the microparticle surface and false positives occurred easily.

Comparative Example 15

Hydrophilized colored cellulose microparticles were prepared using the same method as Example 1. The carboxyl group introduction reaction was subsequently not carried out and the microparticles were used as is as coloring particles. The particle properties and immunochromatographic performance are shown in the following Table 2. Even though the particles were hydrophilized, due to the absence of antibody binding sites, antibodies were unable to be supported on the particles, thereby resulting in extremely low sensitivity.

TABLE 1

| | | Particle Properties | | | | | | |
|---|---|---|---|---|---|---|---|---|
| Run | Composition | Particle diameter nm | Coloring intensity — | Sphericity (L/D) — | Hydrophilic layer | Spacer | Amount of carboxyl groups introduced mmol/g | Amount of residual reactive amino groups mmol/g | Degree of hydrophilization — |
| Example 1 | Cellulose | 338 | 2.3 | 1.5 | Silane layer | (CH2)5 | 0.20 | 0.19 | 58.0 |
| Example 2 | Cellulose | 345 | 2.2 | 1.8 | Silane layer | (CH2)5 | 1.52 | 0.09 | 140.0 |
| Example 3 | Cellulose | 380 | 2.0 | 2.0 | Silane layer | (CH2)5 | 2.87 | 0.00 | 160.0 |
| Example 4 | Cellulose | 405 | 9.6 | 2.5 | Silane layer | (CH2)5 | 1.40 | 0.05 | 138.0 |
| Example 5 | Cellulose | 330 | 2.3 | 1.4 | Silane layer | (CH2)11 | 1.32 | 0.04 | 152.0 |
| Example 6 | Cellulose | 358 | 2.2 | 1.7 | Silane layer | (CH2)18 | 1.43 | 0.08 | 143.0 |
| Example 7 | Cellulose | 409 | 2.1 | 1.9 | Silane layer | C6H4 | 1.01 | 0.12 | 101.0 |
| Example 8 | Cellulose | 879 | 4.5 | 2.4 | Silane layer | (CH2)5 | 1.34 | 0.01 | 145.0 |

TABLE 1-continued

| Run | Composition | Particle diameter | Coloring intensity | Sphericity (L/D) | Hydrophilic layer | Spacer | Amount of carboxyl groups introduced mmol/g | Amount of residual reactive amino groups mmol/g | Degree of hydrophilization |
|---|---|---|---|---|---|---|---|---|---|
| Example 9 | Cellulose | 62 | 1.1 | 1.6 | Silane layer | (CH2)5 | 1.44 | 0.02 | 158.0 |
| Example 10 | Cellulose | 337 | 1.4 | 1.8 | Silane layer | (CH2)2 | 1.80 | 0.01 | 80.0 |
| Example 11 | Cellulose | 529 | 2.1 | 1.9 | Silane layer/ PEG layer | (CH2)11 | 0.30 | 0.02 | 198.0 |
| Example 12 | Cellulose | 321 | 2.2 | 1.3 | PEG layer | (CH2)11 | 1.57 | 0.02 | 174.0 |
| Example 13 | Cellulose | 331 | 2.0 | 1.1 | Silane layer | (CH2)30 | 1.31 | 0.01 | 88.0 |
| Example 14 | Cellulose | 328 | 2.3 | 1.2 | Silane layer | (CH2)5 | 0.12 | 0.02 | 120.0 |
| Example 15 | Cellulose | 321 | 2.6 | 1.9 | Silane layer | (PEG)14 | 1.87 | 0.01 | 98.0 |
| Example 16 | Cellulose | 365 | 2.4 | 1.3 | Silane layer | (CH2)11 | 1.02 | 0.22 | 198.0 |
| Example 17 | Cellulose | 344 | 2.9 | 1.1 | Silane layer | (PEG)14 | 0.13 | 0.02 | 22.0 |
| Example 18 | Cellulose | 367 | 2.1 | 1.8 | Silane layer | (PEG)14 | 1.77 | 0.33 | 189.0 |
| Example 19 | Cellulose | 355 | 2.8 | 1.2 | Silane layer | (CH2)11 | 0.19 | 0.31 | 87.0 |
| Example 20 | Cellulose | 333 | 2.0 | 1.6 | Silane layer | (PEG)14 | 0.10 | 0.24 | 111.0 |
| Example 21 | Cellulose | 321 | 2.3 | 1.4 | Silane layer | (PEG)454 | 1.01 | 0.02 | 122.0 |

| Run | Particle Performance Amount of adsorbed protein wt % | Immunochromatographic Performance ||||| Diagnosis time s | Detection limit mIU |
|---|---|---|---|---|---|---|---|
| | | False Positives |||| | |
| | | Incidence % | Visual grade of false positive specimens* |||| |
| | | | Specimen A | Specimen B | Specimen C | | |
| Example 1 | 1 | 0 | 0 | 0 | 0 | 20 | 0.013 |
| Example 2 | 1 | 0 | 0 | 0 | 0 | 18 | 0.013 |
| Example 3 | 1 | 0 | 0 | 0 | 0 | 17 | 0.013 |
| Example 4 | 1 | 0 | 0 | 0 | 0 | 12 | 0.006 |
| Example 5 | 1 | 0 | 0 | 0 | 0 | 14 | 0.013 |
| Example 6 | 1 | 0 | 0 | 0 | 0 | 14 | 0.013 |
| Example 7 | 1 | 0 | 0 | 0 | 0 | 18 | 0.013 |
| Example 8 | 1 | 0 | 0 | 0 | 0 | 13 | 0.006 |
| Example 9 | 1 | 0 | 0 | 0 | 0 | 35 | 0.013 |
| Example 10 | 1 | 0 | 0 | 0 | 0 | 21 | 0.013 |
| Example 11 | 1 | 0 | 0 | 0 | 0 | 18 | 0.013 |
| Example 12 | 1 | 0 | 0 | 0 | 0 | 16 | 0.013 |
| Example 13 | 1 | 0 | 0 | 0 | 0 | 16 | 0.013 |
| Example 14 | 2 | 1 | 0 | 2 | 0 | 32 | 0.013 |
| Example 15 | 4 | 1 | 0 | 3 | 0 | 28 | 0.025 |
| Example 16 | 4 | 1 | 0 | 3 | 0 | 26 | 0.013 |
| Example 17 | 4 | 1 | 0 | 4 | 0 | 24 | 0.025 |
| Example 18 | 5 | 2 | 0 | 4 | 3 | 33 | 0.025 |
| Example 19 | 3 | 1 | 0 | 3 | 0 | 38 | 0.013 |
| Example 20 | 5 | 2 | 0 | 3 | 3 | 24 | 0.025 |
| Example 21 | 0 | 0 | 0 | 0 | 0 | 38 | 0.025 |

*Visual grade was evaluated to one of eleven grades ranging from 0 to 10, with a larger number representing a darker color.

TABLE 2

| Run | Composition | Particle diameter nm | Coloring intensity | Sphericity (L/D) | Hydrophilic layer | Spacer | Amount of carboxyl groups introduced mmol/g | Amount of residual reactive amino groups mmol/g | Degree of hydrophilization |
|---|---|---|---|---|---|---|---|---|---|
| Comp. Ex. 1 | Cellulose | 330 | 2.5 | 1.3 | None | None | 0.00 | 0.00 | 13.0 |
| Comp. Ex. 2 | Cellulose | 335 | 2.2 | 1.4 | None | (CH2)16 | 0.10 | 0.00 | 16.0 |
| Comp. Ex. 3 | Cellulose | 310 | 2.3 | 1.3 | None | (CH2)5 | 0.21 | 0.00 | 11.0 |
| Comp. Ex. 4 | Cellulose | 320 | 2.4 | 1.2 | None | (CH2)5 | 0.23 | 0.30 | 9.0 |
| Comp. Ex. 5 | Cellulose | 331 | 2.5 | 1.5 | None | (PEG)14 | 0.22 | 0.00 | 15.0 |
| Comp. Ex. 6 | Cellulose | 333 | 2.2 | 1.3 | None | (CH2)11 | 0.11 | 0.25 | 10.0 |
| Comp. Ex. 7 | Cellulose | 341 | 2.1 | 1.1 | None | (PEG)14 | 0.25 | 0.24 | 9.0 |
| Comp. Ex. 8 | Cellulose | 339 | 2.6 | 1.8 | None | (PEG)14 | 0.14 | 0.30 | 8.0 |
| Comp. Ex. 9 | Cellulose | 339 | 0.8 | 1.9 | Silane layer | (CH2)5 | 0.26 | 0.02 | 128.0 |
| Comp. Ex. 10 | Cellulose | 42 | 1.1 | 1.4 | Silane layer | (CH2)5 | 0.31 | 0.11 | 121.0 |
| Comp. Ex. 11 | Cellulose | 330 | 0.1 | 2.9 | Silane layer | (CH2)5 | 0.25 | 0.01 | 15.0 |
| Comp. Ex. 12 | Cellulose | 980 | 2.9 | 2.7 | Silane layer | (CH2)11 | 1.20 | 0.03 | 111.0 |
| Comp. Ex. 13 | Gold colloid | 50 | 1.3 | 2.7 | None | (PEG)68 | 0.09 | 0.00 | 0.1 |
| Comp. Ex. 14 | Latex | 470 | 0.5 | 1.2 | None | Unknown | 0.11 | 0.00 | 1.2 |
| Comp. Ex. 15 | Cellulose | 333 | 2.2 | 1.2 | Silane layer | None | 0.00 | 0.53 | 92.0 |

TABLE 2-continued

| | Particle Performance Amount of adsorbed protein | Immunochromatographic Performance | | | | Diagnosis time | Detection limit |
|---|---|---|---|---|---|---|---|
| | | False positives | | | | | |
| | | Incidence | Visual grade of false Positive specimens* | | | | |
| Run | wt % | % | Specimen A | Specimen B | Specimen C | s | mIU |
| Comp. Ex. 1 | 8 | 3 | 3 | 5 | 4 | 41 | 0.025 |
| Comp. Ex. 2 | 8 | 3 | 3 | 6 | 5 | 39 | 0.013 |
| Comp. Ex. 3 | 7 | 3 | 3 | 4 | 3 | 34 | 0.013 |
| Comp. Ex. 4 | 8 | 3 | 2 | 4 | 4 | 36 | 0.013 |
| Comp. Ex. 5 | 8 | 3 | 3 | 4 | 4 | 32 | 0.013 |
| Comp. Ex. 6 | 8 | 3 | 2 | 4 | 3 | 38 | 0.013 |
| Comp. Ex. 7 | 8 | 3 | 3 | 5 | 5 | 37 | 0.013 |
| Comp. Ex. 8 | 8 | 3 | 4 | 7 | 6 | 42 | 0.013 |
| Comp. Ex. 9 | 2 | 1 | 0 | 1 | 0 | 39 | 0.050 |
| Comp. Ex. 10 | 2 | 1 | 0 | 0 | 1 | 44 | 0.050 |
| Comp. Ex. 11 | N.D. | Considerable decrease in microparticle coloring intensity | | | | | |
| Comp. Ex. 12 | 2 | Poor movement through membrane | | | | | |
| Comp. Ex. 13 | 9 | 4 | 5 | 7 | 5 | 50 | 0.050 |
| Comp. Ex. 14 | 8 | 4 | 6 | 6 | 6 | 45 | 0.050 |
| Comp. Ex. 15 | 1 | 0 | 0 | 0 | 0 | 630 | >1.600 |

** Visual grade was evaluated to one of eleven grades ranging from 0 to 10, with a larger number representing a darker color.

INDUSTRIAL APPLICABILITY

The hydrophilized colored cellulose microparticles according to the present invention enable rapid diagnosis while maintaining high detection sensitivity, and can be preferably used as coloring particles of an immunochromatographic diagnostic kit that surprisingly reduces the risk of the occurrence of false positives.

The invention claimed is:

1. Colored cellulose microparticles having an average particle diameter of 60 nm to 900 nm, having coloring intensity of 1.0 to 10.0, having a hydrophilic layer on the surface of the microparticles, wherein the hydrophilic layer is chemically bonded to hydroxyl groups of the microparticles, having carboxyl groups introduced onto the surface of the microparticles with spacers interposed between the carboxyl groups and the colored cellulose microparticles, wherein the spacers bond with reactive groups of the hydrophilic layer, and the spacers are hydrocarbon-based hydrophobic structures, and wherein the hydrophilic layer has a degree of hydrophilization of 30.0 to 200.0.

2. The colored cellulose microparticles according to claim 1, wherein the amount of the carboxyl groups introduced is 0.20 mmol to 3.00 mmol per gram of the colored cellulose microparticles.

3. The colored cellulose microparticles according to claim 1, wherein the hydrophilic layer is any of a silane layer, a polyethylene glycol (PEG) layer or a mixed layer of a silane layer and a polyethylene glycol (PEG) layer.

4. A structure consisting of a ligand covalently bonded to the carboxyl groups with the colored cellulose microparticles according claim 1.

5. An immunochromatographic diagnostic kit which comprises a conjugate pad containing the structure according to claim 4; a membrane; a sample pad; and an absorbent pad.

* * * * *